(12) United States Patent
Schrøder Glad et al.

(10) Patent No.: US 6,607,902 B2
(45) Date of Patent: Aug. 19, 2003

(54) CELL-WALL DEGRADING ENZYME VARIANTS

(75) Inventors: Sanne O Schrøder Glad, Ballerup (DK); Carsten Andersen, Værløse (DK); Martin Schulein, deceased, late of Copenhagen (DK), by Hanne Dela, legal representative; Torben Peter Frandsen, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/910,505

(22) Filed: Jul. 19, 2001

(65) Prior Publication Data

US 2003/0017575 A1 Jan. 23, 2003

Related U.S. Application Data

(60) Provisional application No. 60/290,724, filed on May 14, 2001.

(30) Foreign Application Priority Data

May 4, 2000 (DK) ........................................ 2001 00705
Jul. 19, 2000 (DK) ........................................ 2000 01117
May 10, 2001 (DK) ........................................ 2001 00734

(51) Int. Cl.[7] ................................................. C12N 9/88
(52) U.S. Cl. ..................... 435/232; 536/23.2; 536/23.1; 435/263; 435/264; 435/267; 510/300
(58) Field of Search ................................ 435/232, 263, 435/264, 267; 536/23.2, 23.1

(56) References Cited

PUBLICATIONS

Keen et al., Journal of Bacteriology, Nov. 1986, p. 595–606, vol. 168. No. 2.
Pickersgill et al., Structure of Biology, vol. 1, No. 10, Oct. 1994, 717–722.
Yoder et al., Science, vol. 260, Jun. 4, 1993, 1503–1507.
Yoder et al., Plant physiol. (1995) 107: 349–364.
Yoder et al., Structure 1993, vol. 1, No. 4, 241–251.
Yoder et al., J. of Bio. Chem., vol. 265, No. 20, 11429–11431, 1990.
Kim et al., J. Mol. Biol . (1989) 208, 365–367.
Lietze et al., Plant Physiol. (1996) 111: 73–92.
Tamaki et al., Journal of Bacteriology, vol. 170, No. 8, pp. 3468–3478, (Aug. 1988).

*Primary Examiner*—Nashaat T. Nashed
(74) *Attorney, Agent, or Firm*—Elias J. Lambiris

(57) ABSTRACT

A variant of a cell-wall degrading enzyme having a beta-helix structure, which variant holds at least one substituent in a position determined by identifying all residues potentially belonging to a stack; characterising the stack as interior or exterior; characterising the stack as polar, hydrophobic or aromatic/heteroaromatic based on the dominating characteristics of the parent or wild-type enzyme stack residues and/or its orientation relative to the beta-helix (interior or exterior); optimizing all stack positions of a stack either to hydrophobic aliphatic amino acids, hydrophobic aromatic or polar amino acids by allowing mutations within one or all positions to amino acids belonging to one of these groups; measuring thermostability of the variants by DSC or an application-related assay such as a Pad-Steam application test; and selecting the stabilized variants. Variant of a wild-type parent pectate lyase (EC 4.2.2.2) having the conserved amino acid residues D111, D141 or E141, D145, K165, R194 and R199 when aligned with the pectate lyase comprising the amino acid sequence of SEQ ID NO: 2 are preferred.

31 Claims, 3 Drawing Sheets

Figures 1, 2, 3:
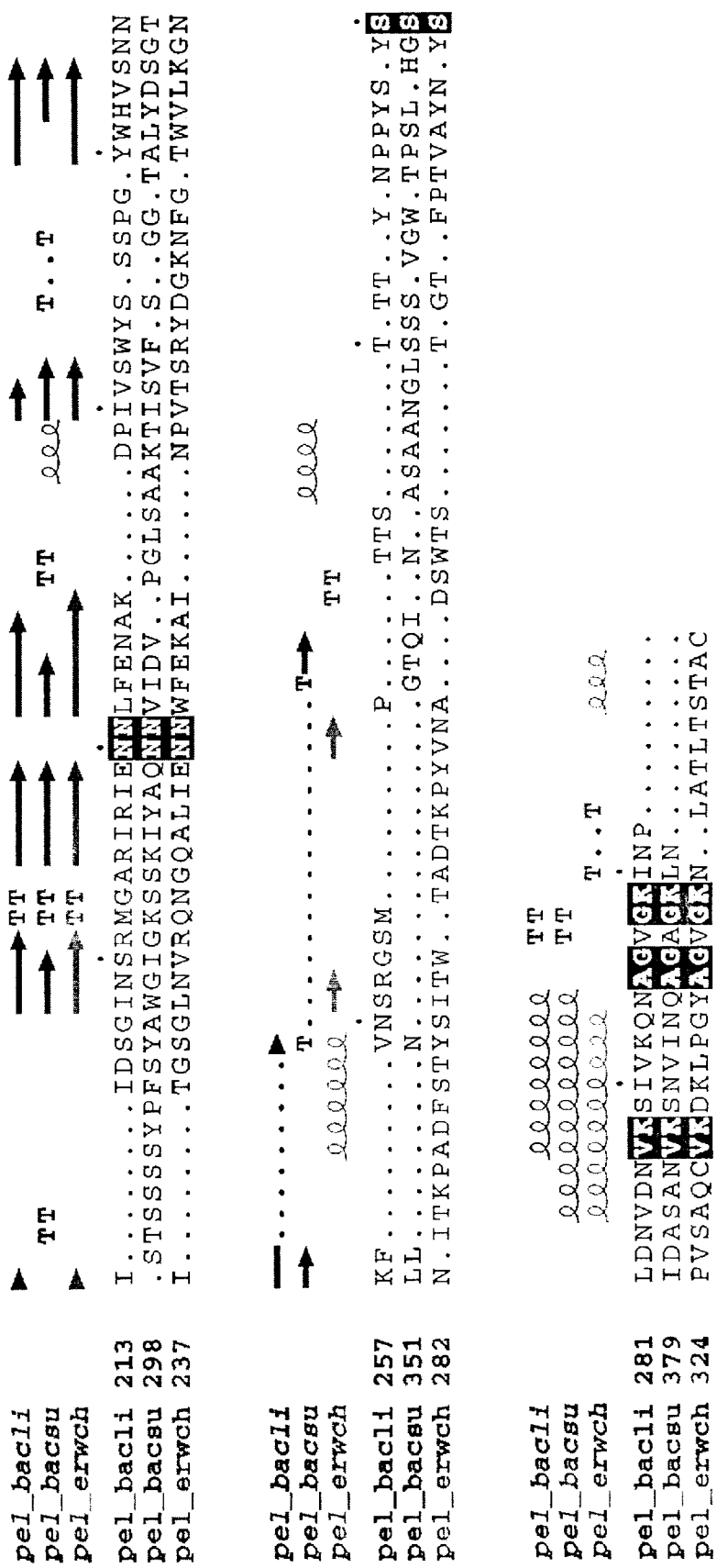

```
pel_bacli          
pel_bacsu          
pel_erwch          
                                                                                      TT
                                              ααα              TT             ααα           αααααααα
                                              ααα              TT             ααα           αααααααα
                                                               TT                           αααααααα
                                                               ↑↑             ↑↑↑
                                                               ↑↑             ↑↑↑
                                                               ↑↑             ↑↑↑
pel_bacli    1     ADFS.........L..KGFAALNGGTTGGEG..G..QTVTVTTGDQLIAALKNKN..
pel_bacsu    1     ..ADLGHQTL..GSN.DGWGAYSTGTTGGSK..ASSSNVYYTVSNRNQLVSALG...KE
pel_erwch    1     ...........ATD..TGGYAA....TAGGNVTGA...VSKATSMQDIVNIIDAA...

TT                    TT                TT
                   T                                                      ↑↑
                                                                          ↑↑
pel_bacli   41     TN..........ANTPLKHYVNGTIT.TSNTS..DDNLKPLGLNDYKDPEYDLDKYLKAYD
pel_bacsu   49     TN.....TT..PKIHYIKCTIDMNV...
pel_erwch   37     .RLDANGKKVKGGA.YPLVHTYTGN..

αααα                        αααααααααα      ααα TT    αααα.α                     ▄▄▄
                                                                                                    ▄▄▄
                                                                                                    ■H■
pel_bacli   60     .PSTWGKKEPSGTQEEARARSQKN.............A.SKIDVKDVS.NVS▄▄▄
pel_bacsu   94     ...................EDSLINAAAANICGQWSKD...QKAR.VMVDI..PA.NTTT
pel_erwch   60     ...................................PRGVEIKEFTKGITT
```

Fig. 1-1

Fig. 1-2

CELL-WALL DEGRADING ENZYME VARIANTS

CROSS-REFERENCE TO RELATED APPLICATIONS

This application claims, under 35 U.S.C. 119, priority of Danish application nos. PA 2000 01117, filed Jul. 19, 2000, PA 2001 00705, filed May 4, 2001, and PA 2001 00734, filed May 10, 2001, and the benefit of U.S. provisional application No. 60/290,724, filed May 14, 2001, the contents of which are fully incorporated herein by reference.

FIELD OF THE INVENTION

The present invention relates to variants of microbial cell-wall degrading enzymes, more specifically to variants of enzymes having a pectinase structure similar to that of Bacillus licheniformis enzymes exhibiting pectate lyase activity as their major enzymatic activity in the neutral and alkaline pH ranges; to a method of producing such enzymes; and to methods for using such enzymes in the textile, detergent and cellulose fiber processing industries. The enzyme variants of the invention may exhibit increased thermostability as compared to the parent enzyme.

BACKGROUND OF THE INVENTION

Plant cell walls consist of a complicated network of fibrous materials. The composition of the cell walls varies considerably, depending on the source of the vegetable material. However, in general its composition can be summarized as mainly comprising non-starch polysaccharides. These polysaccharides can be found in various forms: cellulose, hemicellulose and pectins.

The composition of a plant cell wall is both complex and variable. Polysaccharides are mainly found in the form of long chains of cellulose (the main structural component of the plant cell wall), hemicellulose (comprising e.g. various .beta.-xylan chains) and pectin. The occurrence, distribution and structural features of plant cell wall polysaccharides are determined by: 1. Plant species; 2. Variety; 3. Tissue type; 4. Growth conditions; and 5. Ageing (Chesson (1987), Recent Advances in Animal Food Nutrition, Haresign on Cole, eds.). Butterworth, London, 71–89).

Basic differences exist between monocotyledons (e.g. cereals and grasses) and dicotyledons (e.g. clover, rapeseed and soybean) and between the seed and vegetative parts of the plant (Carre' and Brillouet (1986), Science and Food Agric. 37, 341–351). Monocotyledons are characterized by the presence of an arabinoxylan complex as the major hemicellulose backbone. The main structure of hemicellulose in dicotyledons is a xyloglucan complex. Moreover, higher pectin concentrations are found in dicotyledons than in monocotyledons. Seeds are generally very high in pectic substances, but relatively low in cellulosic material. Three more or less interacting polysaccharide structures can be distinguished in the cell wall:

1. The middle lamella forms the exterior cell wall. It also serves as the point of attachment for the individual cells to one another within the plant tissue matrix. The middle lamella consists primarily of calcium salts of highly esterified pectins;
2. The primary wall is situated just inside the middle lamella. It is a well-organized structure of cellulose microfibrils embedded in an amorphous matrix of pectin, hemicellulose, phenolic esters and proteins;
3. The secondary wall is formed as the plant matures.

During the plant's growth and ageing phase, cellulose microfibrils, hemicellulose and lignin are deposited.

There is a high degree of interaction between cellulose, hemicellulose and pectin in the cell wall. The enzymatic degradation of these rather intensively cross-linked polysaccharide structures is not a simple process. A large number of enzymes are known to be involved in the degradation of plant cell walls. They can broadly be subdivided in cellulases, hemicellulases and pectinases (Ward and Young (1989), CRC Critical Rev. in Biotech. 8, 237–274).

Cellulose is the major polysaccharide component of plant cell walls. It consists of .beta. 1,4 linked glucose polymers.

Cellulose can be broken down by cellulases, also called cellulolytic enzymes. Cellulolytic enzymes have been divided traditionally into three classes: endoglucanases, exoglucanases or cellobichydrolases and .beta.-glucosidases (Knowles, J., et al. (1987), TIBTECH 5, 255–261). Like all cell wall degrading enzymes they can be produced by a large number of bacteria, yeasts and fungi. Apart from cellulases degrading .beta.-1,4 glucose polymers, endo-1,3/1,4 beta.-glucanases and xyloglucanases should be mentioned (Ward and Young op. cit.).

Pectins are major constituents of the cell walls of edible parts of fruits and vegetables. The middle lamella which are situated between the cell walls are mainly built up from protopectin which is the insoluble form of pectin. Pectins are considered as intracellular adhesives and due to their colloidal nature they also have an important function in the water regulation system of plants. The amount of pectin can be very high. For example, lemon peels are reported to contain pectin at up to 30% of their dry weight, orange peels contain from 15–20% and apple peels about 10% (Norz, K. (1985). Zucker und Susswaren Wirtschaft 38, 5–6).

Pectins are composed of a rhamno-galacturonan backbone in which 1,4-linked (.alpha.-D-galacturonan chains are interrupted at intervals by the insertion of 1,2-linked (.alpha.-L-rhamnopyranosyl residues (Pilnik, W. and A. Voragen (1970), In: The Biochemistry of fruits and their products, vol. 1, Chapter 3, p. 53. Acad. Press). Other sugars, such as D-galactose, L-arabinose and D-xylose, are present as side chains. A large part of the galacturonan residues is esterified with methyl groups at the C2 and C3 position.

A large number of enzymes are known to degrade pectins. Examples of such enzymes are pectin esterase, pectin lyase (also called pectin transeliminase), pectate lyase, and endo- or exo-polygalacturonase (Pilnik and Voragen (1990). Food Biotech 4, 319–328). Apart from enzymes degrading smooth regions, enzymes degrading hairy regions such as rhamnogalacturonase and accesory enzymes have also been found (Schols et al. (1990), Carbohydrate Res. 206, 105–115; Searle Van Leeuwen et al. (1992). Appl. Microbiol. Biotechn. 38, 347–349).

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Pectate lyases degrade un-methylated (polygalacturonate) or low-methylated pectin by β-elimination of the α-1,4-glycosidic bond. The enzymes are generally characterised by an alkaline pH optimum, an absolute requirement for $Ca^{2+}$ (though its role in binding and catalysis is unknown) and good temperature stability.

Pectate lyases have been cloned from different bacterial genera such as Bacillus, Erwinia, Pseudomonas, Klebsiella and Xanthomonas.

U.S. Pat. No. 6,124,127, which is hereby incorporated by reference in its entirety, discloses a cloned *Bacillus licheniformis* pectate lyase. The DNA sequence encoding this *B. licheniformis* pectate lyase and the deduced amino acid sequence are listed in the appended sequence listing as SEQ ID NOS. 1 and 2, respectively.

The crystal structures of pectate lyases of *Bacillus subtilis* (1BN8[1] (and an R279K mutant, 2BSP[2])), of *Erwinia chrysanthemi* (PelC: 2PEC[3]/1AIR[4]; PelC (R218K) in complex with substrate: ref 10; and PelE: 1PCL[5]), of *Erwinia carotovora* (PelC: 1PLU[6]), and of Bacillus sp. strain 2 KSM-P15 (1EE6) have been published. In addition, the crystal structures of the structurally very similar pectin lyases from *Aspergillus niger* (PlyA:1IDJ[7]/1IDK[7] and PlyB:1QCX[8]) and of the polygalacturonase from *Erwinia carotovora* (1BHE[9]) are also known (1: R. Pickersgill, J. Jenkins, G. Harris, W. Nasser, J. Robert-Baudrouy; *Nat.Struct.Biol.* 1994, 1, 717;

2: R. Pickersgill, K. Worboys, M. Scott, N. Cummings, A. Cooper, J. Jenkins, D. Smith To Be Published;
3: M. D. Yoder, S. E. Lietzke, F. Jurnak; *Structure,* 1993, 1, 241;
4: M. D. Yoder, N. T. Keen, F. Jurnak; *Science,* 1993, 260, 1503;
5: M. D. Yoder, C. A. Dechaine, F. Jurnak; *J. Biol.Chem.* 1990, 265, 11429;
6: S. J. Tamaki, S. Gold, M. Robeson, S. Manulis, N. T. Keen; *J Bacteriol.* 1988, 170, 3468;
7: S. E. Lietzke, R. D. Scavetta, M. D. Yoder, F. A. Jurnak; *Plant Physiol.* 1996, 111, 73;
8: S. E. Lietzke, N. T. Keen, F. Jurnak; To Be Published;
9: Y. Kim, V. Mosser, N. Keen, F. Jurnak; *J.Mol.Biol.* 1989, 208, 365; N. T. Keen, S. Tamaki; *J. Bacteriol.* 1986, 168, 595;
10: M. D. Yoder, F. A. Jurnak; Plant Physiol. 1995, 107, 349;
11: O. Mayans, M. Scott, I. Connerton, T. Gravesen, J. Benen, J. Visser, R. Pickersgill, J. Jenkins; *Structure,* 1997, 5, 677;
12: J. Vitali, B. Schick, H. C. M. Kester, J. Visser, F. Jurnak; *Plant Physiol.* 1998, 116, 69;
13: R. Pickersgill, D. Smith, K. Worboys, J. Jenkins; *J Biol. Chem.* 1998, 273, 24660;
14: R. D. Scavetta, S. R. Herron, A. T. Hotchkiss, N. Kita, N. T. Keen, J. A. E. Benen, H. C. M. Kester, J. Visser, F. Jurnak; *Plant Cell* 1999, 11, 1081;
15: M. Akita, A. Suzuki, T. Kobayashi,S. Ito, T. Yamane Crystallization And Preliminary X-Ray Analysis Of 2 High-Alkaline Pectate Lyase Acta Crystallogr., Sect.D V. 56 749 2000).

The crystal structures of a pectin methyl esterase (1QJV; Jenkins, J.; Mayans, O.; Smith, D.; Worboys, K.; Pickersgill, R. W. Journal of Molecular Biology, vol 305, 2001, 951–960) and a rhamnogalacturonase (1RMG; Petersen, T. N., Kauppinen, S., Larsen, S.: The crystal structure of rhamnogalacturonase A from *Aspergillus aculeatus*: a right-handed parallel beta helix. *Structure* 5 pp. 533 (1997)) have also been published.

Pectinases consist of an unusual backbone of parallel β-strands coiled in a large right-handed helix. The parallel β-helix contains three β-strands pr. turn (PB1, PB2, and PB3) and consecutive turns stack one on to another to form a super-helix. Two of the β-sheets form a β-sandwich folded against each other in an anti-parallel manner. The third parallel β-sheet is perpendicular to the β-sandwich, resulting in an L-shaped cross-section. There is no direct sequence repetition in the β-helix, however a typical characteristic of the domain is that the side-chains of residues at corresponding positions in consecutive β-strands stack directly upon each other. The stacks can be of aliphatic (typically leucine, isoleucine and valine residues), hydrogen-bonded (typically asparagine residues, known as an asparagine ladder), or aromatic (typically tyrosine and phenylalanine residues) character. Stack amino acid side chains are found both within and outside the parallel β-helix, forming a linear arrangement parallel to the axis of the β helix.

The three β-sheets are separated by turns, termed T1 (between PB1 and PB2), T2 (between PB2 and PB3, introducing a 90° change of backbone orientation), and T3 (between PB3 and PB1). It is within these regions that the largest diversity among the different pectinases is found, the most conserved regions being the β-sheets PB2 and PB3 and the T2 turn. There is a large variety in the length of these turns, ranging from only two amino acids to tens of amino acids. The T3 turns are commonly lengthy and of more complex formation and constitute a loop region which together with the β-helix (primarily PB1) confines the substrate binding crevice.

The N-terminal end of the parallel β-helix domain is capped by an α-helix that is structurally conserved although the sequence conservation is undetectable. The C-terminal end of the β-helix is terminated by a loop structure with no specific conservation. The N-terminal tail packs against PB2 while the C-terminal tail lies across PB2 ending in a highly structurally (but not sequentially) conserved, amphipathic α-helix, with the hydrophobic part packing against the T2 turn.

In the bottom of the pronounced substrate-binding cleft calcium binds to three aspartate residues, two of which are conserved for all pectate lyases and one that can also be glutamate. In addition, two arginines, one lysine and a proline all facing the substrate-binding cleft are conserved in the pectinase family. Mutation of the aspartates (one can be mutated to glutamate), the arginines or the lysine destroys the catalytic activity, however the exact catalytic mechanism is not fully understood.

A second cluster of invariant amino acids in the pectate lyases is located practically opposite to the $Ca^{2+}$-binding site, that is, on the other side of the β-helix domain packing against the N-terminus. Even though this iWiDH region (SEQ ID NO: 27) is highly conserved throughout the pectinase family, the function of this is as yet unknown. It does not seem to be important for pectinolytic cleavage, but has been speculated to be involved in a second, yet unidentified, enzymatic function, or to be of importance in secretion of the enzyme always being of extra-cellular origin.

Hemicelluloses are the most complex group of non-starch polysaccharides in the plant cell wall. They consist of polymers of xylose, arabinose, galactose or mannose which are often highly branched and connected to other cell wall structures. Thus a multitude of enzymes is needed to degrade these structures (Ward and Young op.cit.). Xylanase, galactanase, arabinanase, lichenase and mannanase are some hemicellulose degrading enzymes.

Endo- and exo-xylanases and accessory enzymes such as glucuronidases, arabinofuranosidases, acetyl xylan esterase and ferulic acid or coumaric acid esterase have been summarized by Kormelink (1992, Ph.D.-thesis, University of Wageningen, The Netherlands). They are produced by a wide variety of micro-organisms and have varying temperature and pH optima.

Like other cell wall degrading enzymes (CWDE'S) galactanases occur in many micro-organisms (Dekker and Richards (1976), Adv. Carbohydrat. Chem. Biochem. 32, 278–319). In plant cell walls two types of arabinogalactans are present: type I 1,4 .beta.-galactans and type II 1,3/1,6 .beta.-galactans which have a branched backbone (Stephen (1983). In: The Polysaccharides. G. O. Aspinael (ed.). Ac. Press, New York, pp. 97–193). Both types of galactans require their own type of endo enzyme to be degraded. It can be expected that other enzymes, such as arabinan-degrading enzymes and exo-galactanases play a role in the degradation of arabinogalactans.

The hemicellulose 1,3-1,4-.beta.-glucan is a cell wall component present in cereal (barley, oat, wheat and rye) endosperm. The amount of .beta.-glucan in cereal endosperm varies between 0.7–8%. It is an unbranched polysaccharide built from cellotriose and cellotetraose residues linked by a 1,3-glucosidic bond. The ratio tri/tetra saccharose lies between 1.9 and 3.5.

Lichenase (EC 3.2.1.73) hydrolyse 1,4-beta-D-glucosidic linkages in beta-D-glucans containing 1,3- and 1,4-bonds. Lichenase reacts not on beta-D-glucans containing only 1,4-bonds such as for example in cellulose. Thus, damage of cellulose fibers in fabrics does not occur by the application of lichenase. Lichenases are produced by bacteria like *B. amyloliguefaciens, B. circulans, B. licheniformis* and plants (Bielecki S. et al. Crit. Rev. in Biotechn. 10(4), 1991, 275–304).

Arabinans consist of a main chain of .alpha.-L-arabinose subunits linked (.alpha.-(1->5) to another. Side chains are linked .alpha.-(1->3) or sometimes .alpha.-(1->2) to the main alpha.-(1->5)-L-arabinan backbone. In apple, for example, one third of the total arabinose is present in the side chains. The molecular weight of arabinan is normally about 15 kDa.

Arabinan-degrading enzymes are known to be produced by a variety of plants and micro-organisms. Three enzymes obtainable from *A.niger* have been cloned by molecular biological techniques (EP-A-506190). Also arabinosidase from bacteria such as Bacteroides has been cloned (Whitehead and Hespell (1990). J. Bacteriol. 172, 2408).

Galactomannans are storage polysaccharides found in the seeds of Leguminosae. Galactomannans have a linear (1→4)-.beta.-mannan backbone and are substituted with single (1→6).alpha.-galactose residues. For example in guar gum the ratio mannose/galactose is about 2 to 1. Galactomannans are applied as thickeners in food products like dressings and soups.

Mannanase enzymes are described in PCT application WO 93/24622.

Glucomannan consists of a main chain of glucose and mannose. The main chain may be substituted with galactose and acetyl groups; mannanases can be produced by a number of microorganisms, including bacteria and fungi.

To summarise, it can be said that a large number of plant cell wall degrading enzymes exist, produced by different organisms. Depending on their source the enzymes differ in substrate specificity, pH and temperature optima, $V_{max}$, $K_m$ etc. The complexity of the enzymes reflects the complex nature of plant cell walls, which differ strongly between plant species and within species between plant tissues.

It is an object of the present invention to provide a cell-wall degrading enzyme variant, especially a pectin degrading enzyme variant, which exhibits improved performance over the known microbial cell-wall degrading enzymes when applied e.g. in detergents or in textile industry processes.

SUMMARY OF THE INVENTION

The inventors have now found that certain amino acid substitutions in cell-wall degrading enzymes having a structure including a β-helix result in enzyme variants having improved performance in the neutral or alkaline pH range, especially improved thermostability when determined by DSC (Disc Scanning Calorimetry) or by a Pad-Steam application test.

In a preferred embodiment of the invention, variants of the *Bacillus licheniformis* pectate lyase (EC 4.2.2.2) encoded by SEQ ID NO: 1 exhibit improved properties over the parent pectate lyase, the improved properties being advantageous when the enzyme is applied industrially. The inventors have provided such variants by having succeeded in identifying certain positions in the protein sequence in which positions the naturally occurring amino acid residue may be substituted or deleted or in which positions one or more amino acid residues may be inserted with the purpose of providing an improved pectate lyase variant, and have further provided a method of constructing cell-wall degrading enzyme variants with improved performance in industrial applications.

Accordingly, in a first aspect the present invention relates to a variant of a cell-wall degrading enzyme having a beta-helix structure, which variant holds at least one substituent in a position determined by (i) identifying all residues potentially belonging to a stack; (ii) characterising the stack as interior or exterior; (iii) characterising the stack as polar (typically asparagine, serine, threonine) or hydrophobic (either aliphatic: leucine, isoleucine or valine; or aromatic/heteroaromatic: phenylalanine, tyrosine, histidine, and less often tryptophan) based on the dominating characteristics of the parent or wild-type enzyme stack residues and/or its orientation relative to the beta-helix (interior or exterior); (iv) optimising all stack positions of a stack either to hydrophobic aliphatic amino acids, hydrophobic aromatic/heteroaromatic amino acids (preferably histidine alone, tyrosine and phenylalanine alone or in combination) or polar amino acids (preferably asparagine) by allowing mutations within one or all positions to amino acids belonging to one of these groups; (v) measuring thermostability of the variants by DSC or an application-related assay such as a Pad-Steam application test; and (vi) selecting the stabilized variants. Alternatively, the variants may be provided by scanning the X-ray structure for positions that may be mutated into a proline residue; and mutating at least one of these positions into a proline; or by scanning the x-ray structure for positions that may be mutated into cysteine residues in order for these to form disulfide bridges and thereby stabilize the structure; and mutate at least one of these positions into a cysteine; or by initiating molecular dynamics calculations specifying different temperatures using the x-ray structure.

In a preferred embodiment, the invention relates to a variant of a wild-type parent pectate lyase (EC 4.2.2.2) having the conserved amino acid residues D111, D141 or E141, D145, K165, R194 and R199, optionally also W123, D125 and H126, when aligned with the pectate lyase comprising the amino acid sequence of SEQ ID NO: 2, in which the variant is substituted in at least one position selected from the group consisting of the positions 41, 55, 71, 72, 82, 83, 90, 100, 102, 114, 129, 133, 136, 144, 160, 163, 167, 168, 169, 189, 192, 197, 198, 200, 203, 207, 220, 222, 230, 232, 236, 237, 238, 244, 246, 261, 262, 265, 269, 282, 283, 284, 285, 288 and 289. It is believed that the novel enzyme will be classified according to the Enzyme Nomenclature in the Enzyme Class EC 4.2.2.2. However, it should be noted that it is contemplated that the pectate lyase variant of the invention also exhibits catalytic activity on pectin (which may be esterified) besides the activity on pectate and polygalacturonides conventionally attributed to enzymes belonging to EC 4.2.2.2.

Within another aspect, the present invention provides an isolated polynucleotide molecule prepared from the DNA molecule comprising the DNA sequence of SEQ ID NO: 1 by conventional methods such as site-directed mutagenesis.

Within yet another aspect of the invention there is provided an expression vector comprising the following operably linked elements: (a) a transcription promoter, (b) the polynucleotide molecule of the invention, (c) degenerate nucleotide sequences of (a) or (b); and a transcription terminator.

Within yet another aspect of the present invention there is provided a cultured cell into which has been introduced an expression vector as disclosed above, wherein said cell expresses the polypeptide encoded by the DNA segment.

Within another aspect of the present invention there is provided an enzyme composition comprising the pectate lyase variant of the invention in combination with other enzymes.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

In comparison with the wild-type cell-wall degrading enzyme, especially a wild-type pectate lyase, it is contemplated that the variant of the invention exhibits increased thermal stability, either due to further stabilization of the β-helix structure of the protein by amino acid substitution in positions within the aliphatic and aromatic stacks of amino acid side chains, or to further stabilization of the binding cleft or the C-terminal turn. Increased thermostability of an enzyme is indeed very useful in many industrial applications which advantageously can be carried out at a temperature above the temperature optimum for the enzymatic activity of the wild-type enzyme.

The cell-wall degrading enzyme variant of the invention is useful for the treatment of cellulosic material, especially cellulose-containing fiber, yarn, woven or non-woven fabric, treatment of mechanical paper-making pulps or recycled waste paper, and for retting of fibres. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme variant having substantial cell-wall degrading activity; and to use of the enzyme variant of the invention for the treatment of cellulose-containing fibers, yarn, woven or non-woven fabric.

The enzyme variant of the invention, especially the pectate lyase variant, is very effective for use in an enzymatic scouring process in the preparation of cellulosic material e.g. for proper response in subsequent dyeing operations.

THE DRAWING

FIGS. 1A–1C are a multiple sequence alignment of pectate lyases derived from *Bacillus licheniformis* (pel_bacli) (SEQ ID NO: 2), *Bacillus subtilis* (pel_bacsu) (SEQ ID NO: 17), and *Erwinia chrysanthemi* (pel_erwch) (SEQ ID NO: 18). The sequences were aligned using the align3d method of Modeller 5o (Ali, A.; T. L. Blundell, "Definition of general topological equivalence in protein structures: A procedure involving comparison of properties and relationships through simulated annealing and dynamic programming," *J. Mol. Biol.*, 212, 403–428 (1990)) module of the Insight 2000 molecular modelling package (Biosym Inc.). Default parameters were employed using simple alignment of the sequences and the public PDB files as well as the one enclosed here. The figure was produced using the program ESPript (Gouet, P., Courcelle, E., Stuart, D. and Metoz, F. *Bioinformatics*, 15, 305–308 (1999)), employing the Blosum matrix.

Appendix 1 shows the structural coordinates of the *Bacillus licheniformis* pectate lyase comprising the amino acid sequence of SEQ ID NO: 2.

DETAILED DESCRIPTION OF THE INVENTION

Protein Numbering

In the context of this invention, a specific numbering of amino acid residue positions in cell-wall degrading enzymes, especially pectate lyase enzymes, is employed. For example, by aligning the amino acid sequences of known pectate lyases it is possible to unambiguously allot an amino acid position number to any amino acid residue in any pectate lyase enzyme, if its amino acid sequence is known.

In FIG. 1, a number of selected amino acid sequences of pectate lyases of different microbial origin are aligned.

Using the numbering system originating from the amino acid sequence of the pectate lyase obtained from the strain *Bacillus licheniformis*, ATCC 14580, disclosed in SEQ ID NO: 2, aligned with the amino acid sequence of a number of other pectate lyases, it is possible to indicate the position of an amino acid residue in a pectate lyase enzyme unambiguously.

In describing the various cell-wall degrading enzyme variants produced or contemplated according to this invention, the following nomenclatures are adapted for ease of reference:

[Original amino acid; Position; Substituted amino acid]

Accordingly, the substitution of serine with isoleucine in position 72 is designated as S72I.

Multiple mutations are separation by addition marks ("+"), e.g. M169I+F198V, representing mutations in positions 169 and 198 substituting methionine (M) with isoleucine (I), and phenylalanine (F) with valine (V), respectively.

All positions referred to herein by pectate lyase numbering refer, unless otherwise stated, to the numbering described above, and are determined relative to the amino acid sequence of the pectate lyase derived from *Bacillus licheniformis*, ATCC 14580.

Definitions

Prior to discussing this invention in further detail, the following terms will first be defined.

The term "wild-type enzyme" denotes an enzyme, which is endogenous to a naturally occurring microorganism such as a fungus or a bacterium found in Nature.

The term "ortholog" (or "species homolog") denotes polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector existing as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinant expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "pectin" denotes pectate, polygalacturonic acid, and pectin which may be esterified to a higher or lower degree.

The term "pectinase" denotes a pectinase enzyme defined according to the art where pectinases are a group of enzymes that cleave glycosidic linkages of pectic substances mainly poly(1,4-alpha-D-galacturonide and its derivatives (see reference Sakai et al., Pectin, pectinase and protopectinase: production, properties and applications, pp 213–294 in: Advances in Applied Microbiology vol:39,1993).

Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase.

The term "thermostability" or "thermal stability" is intended to mean the stability of the protein to thermal influence. All enzyme proteins destabilizes and eventually degrades with increasing temperature, each enzyme protein having a certain temperature range wherein the protein is stable and retains its enzymatic activity. Increased thermostability means that the enzyme protein may retain its enzymatic activity and/or exhibit a higher relative activity at increased temperatures.

How to Use a Sequence of the Invention to Get Other Related Sequences

The disclosed sequence information herein relating to a polynucleotide sequence encoding a wild-type pectate lyase can be used as a tool to identify other homologous pectate lyases. For instance, polymerase chain reaction (PCR) can be used to amplify sequences encoding other homologous pectate lyases from a variety of microbial sources, in particular of different Bacillus species.

Assay for Activity Test

A polypeptide variant of the invention having pectate lyase activity may be tested for pectate lyase activity according to standard test procedures known in the art, such as by applying a solution to be tested to 4 mm diameter holes punched out in agar plates containing 0.2% AZCL galactan (Megazyme, Australia).

Enzyme Variants and the Construction Thereof

In a preferred embodiment, the invention provides a variant of a parent cell-wall degrading enzymes having a β-helix structure, especially a pectate lyase (EC 4.2.2.2) variant, which retains the major enzymatic activity of the parent enzyme and has improved performance in industrial applications; and a method of constructing the variant. Thermostability and detergent compatibility are examples of enzyme properties, which may influence the performance of the enzyme in industrial applications such as commercial and domestic laundering of textiles and treatment of new textile fabric.

The method of constructing the variants of the invention comprises the steps of i) analyzing the structure of the parent enzyme in order to identify at least one amino acid residue or at least one structural part of the parent enzyme which is believed to influence the enzymatic properties of the parent enzyme as evaluated on the basis of structural or functional considerations, ii) constructing a variant which, compared to the parent enzyme, has been modified in the amino acid residue or structural part identified in i) so as to improve performance of the enzyme in textile applications, and, optionally, iii) testing the performance of the enzyme variant.

A model structure can be created using the "model" routine of Modeller 5o (ali, A.; T. L. Blundell, "Definition of general topological equivalence in protein structures: A procedure involving comparison of properties and relationships through simulated annealing and dynamic programming," *J. Mol. Biol.,* 212, 403–428 (1990)) module of the Insight 2000 molecular modelling package (Biosym Inc.). Required input is a sequence alignment in pir format of the protein to be modelled to one or more homologues sequences where the crystal structure is available. The sequence alignment can be calculated by using ClustalW/ClustalX and standard parameters (ClustalX: Thompson,J. D., Gibson,T. J., Plewniak,F., Jeanmougin,F. and Higgins,D. G. (1997) The ClustalX windows interface: flexible strategies for multiple sequence alignment aided by quality analysis tools. Nucleic Acids Research, 24:4876–4882. ClustalW: Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680.). Different refinement levels are determined by the MD_LEVEL keyword, and can typically be set to refine2 (default is less laborious and can also be employed). If further refinements are necessary this can be fulfilled by a minimisation of the structure using a molecular dynamics program such as CHARMm (Brooks et al, J. Computational Chemistry 4, 187 (1983)) possibly subjected to a (short) dynamics run followed by a second minimisation.

The inventors have found that cell-wall degrading enzyme variants, especially pectate lyases variants, having a stabilized beta-helix structure may exhibit improved performance in textile applications. In a preferred embodiment of the invention, the stabilized beta-helix structure may be obtained by determining the stack residues of the parent enzyme, followed by substitution of one or more stack residues. For example, the stack positions may be optimised by:

(i) Identifying all residues potentially belonging to a stack (the stack-residue positions for the *Bacillus licheniformis* pectate lyase comprising the amino acid sequence of SEQ ID NO: 2 are identified below);

(ii) Characterising the stack as interior or exterior;

(iii) Characterising the stack as polar (typically asparagine, glutamine, serine, threonine) or hydrophobic (either aliphatic: leucine, isoleucine or valine; or aromatic/heteroaromatic: phenylalanine, tyrosine, histidine, and less often tryptophan) based on the dominating characteristics of the parent or wild-type enzyme stack residues and/or its orientation relative to the beta-helix (interior or exterior);

(iv) Optimising all stack positions of a stack either to hydrophobic aliphatic amino acids, hydrophobic aromatic amino acids (preferably histidine alone, tyrosine and phenylalanine alone or in combination) or polar amino acids (preferably asparagine) by allowing mutations within one or all positions to amino acids belonging to one of these groups;

(v) Measuring thermostability of the variants by DSC or an application-related assay such as a Pad-Steam application test; and (vi) Selecting the stabilized variants.

A stack residue is defined as one of the following, based on the X-ray crystallography structure of the enzyme or a high-quality homology-build model:

(i) A residue of a β-strand (according to the output of the DSSP program, version July 1995 (Kabsch, W. and Sander, C., Biopolymers 22 (1983), 2577–2637), which β-strand is part of a sheet composed of more than two β-strands; or (ii) A residue without secondary structure but which is linking two β-sheet regions horizontally; or (iii) A residue of a T2 turn composed by no more than two amino acid residues; or (iv) A residue having a $C_\alpha$-atom in line with an already determined stack (i.e. visually it is clearly part of the stack); or (v) A residue which, upon alignment of the amino acid sequence with SEQ ID NO: 2 or the structure as defined by the structural coordinates of Appendix 1, has a stack residue position as defined for the pectate lyase enzyme of SEQ ID NO:2.

Based on this procedure, the following residues are identified as stack-residues in the *Bacillus licheniformis* pectate lyase comprising the amino acid sequence of SEQ ID NO:2 and having the structural coordinates (X-ray structure) disclosed in Appendix 1:

Q22, T23, V24, T25, L45, K46, I47, Y48, T52, I53, T54, I63, D64, V65, K66, V68, S69, N70, V71, S72, I73, V74, E81, L82, K83, I87, K88, I89, W90, A92, N93, N94, I95, I96, I97, R98, N99, L100, K101, I102, H103, E104, I113, G114, I115, E116, S119, K120, N121, I122, W123, V124, D125, H126, N127, E128, I129, Y130, F144, D145, V146, K147, A150, E151, Y152, I153, T154, F155, S156, W157, N158, Y159, V160, H161, D162, G163, M167, L168, M169, T180, I181, T182, F183, H184, H185, N186, W187, F188, E189, N190, L191, P196, S197, F198,E202, G203, H204, I205, Y206,N207,N208, Y209,

F210, N211, K212, I213, I218, N219, S220, R225, I226, R227, I228, E229, N230, N231, L232, F233, E234, N235, A236, I240, V241, Y250, W251, H252, V253, S254, N255, N256, K257, F258, V259, N260, S261

Preferred stack positions for substitution are:
155, 183, 23, 46, 72, 96, 123, 154, 182, 204, 227, 252, 22, 45, 203, 251, 152, 180, 202, 225, 250, 69, 93, 120, 151, 68, 92, 119, 150, 66, 90, 116, 147, 169, 198, 220, 64, 88, 114, 168, 197, 219, 241, 144, 167, 163, 191, 213, 236, 261, 104, 162, 190, 212, 235, 260, 54, 83, 103, 130, 161, 189, 211, 234, 259, 52, 81, 101, 128, 159, 187, 209, 232, 257, 100, 126, 157, 185, 25, 48, 74, 98, 125, 156, 184, 206, 229 and 254.

In another preferred embodiment of the invention, the stabilized beta-helix structure may be obtained by scanning the x-ray structure for positions that may be mutated into a proline residue; this can e.g. be done using the SUGPRO routine in the modelling program Whatif or by the method described in the international patent application published as WO92/19726.

Using the X-ray structure of Appendix 1, i.e. of the native *Bacillus licheniformis* pectate lyase, the following proline positions and proline substitution positions were identified by using the Whatif program:

| 40  | (40)  | ASN |   | 22.03 | --> | 1.34  | ** |
|-----|-------|-----|---|-------|-----|-------|------|
| 41  | (41)  | ALA | T | 25.49 | --> | 0.63  | ** |
| 44  | (44)  | PRO |   | 11.11 | --> | 0.49  | * |
| 55  | (55)  | THR | T | 22.74 | --> | 0.83  | ** |
| 64  | (64)  | ASP | S | 13.24 | --> | 0.21  | * |
| 118 | (118) | PRO | T | 19.36 | --> | -0.39 | * |
| 133 | (133) | LEU | T | 11.74 | --> | -0.11 | * |
| 136 | (136) | ASP |   | 28.31 | --> | 2.25  | *** |
| 137 | (137) | LYS | T | 28.09 | --> | 0.42  | * |
| 164 | (164) | TRP | S | 21.92 | --> | 0.14  | * |
| 173 | (173) | ASP | T | 12.66 | --> | -0.46 | * |
| 196 | (196) | PRO | T | 0.70  | --> | 1.43  | ** |
| 239 | (239) | PRO |   | 0.00  | --> | 0.54  | ** |
| 248 | (248) | PRO |   | 25.11 | --> | -0.13 | * |
| 269 | (269) | SER |   | 15.16 | --> | 0.72  | ** |
| 275 | (275) | PRO |   | 3.83  | --> | 0.77  | ** |
| 283 | (283) | ASN |   | 27.33 | --> | 3.82  | ***** |
| 284 | (284) | VAL | T | 3.11  | --> | 0.99  | ** |
| 288 | (288) | LYS | H | 22.93 | --> | 0.43  | * |
| 289 | (289) | SER | H | 18.98 | --> | 1.11  | ** |

Using the X-ray structure of Appendix 1, i.e. of the native *Bacillus licheniformis* pectate lyase, the following proline positions and proline substitution positions were identified by using the angle algorithm disclosed in WO92/19726 (at which position(s) the dihedral angles φ (phi) constitute values within the interval [−90°<φ<−40°], preferably the dihedral angles φ (phi) and ψ (psi) constitute values within the intervals [−90°<φ<−40°] and [−180°<ψ<−150° or −80 <ψ<10 or 100<ψ<180], and which position(s) is/are not located in regions in which the enzyme is characterized by possessing α-helical or β-sheet structure):

| 5   | L | -65.6 | 129.0 |   |
|-----|---|-------|-------|---|
| 8   | F | -50.9 | -30.9 | G |
| 9   | A | -74.9 | -10.7 | G |
| 10  | A | -86.6 | -9.4  | G |
| 19  | E | -69.7 | 144.2 | T |
| 38  | N | -76.3 | 8.5   | T |
| 39  | K | -68.2 | 133.5 |   |
| 40  | N | -81.8 | 117.6 |   |
| 41  | A | -53.6 | -21.7 | T |
| 44  | P | -63.2 | 146.0 |   |
| 55  | T | -70.5 | -19.8 | S |
| 56  | S | -73.8 | -32.8 | T |
| 59  | S | -81.7 | 7.2   | S |
| 61  | S | -80.3 | -8.8  | S |
| 109 | D | -76.1 | -6.3  | T |
| 112 | A | -64.5 | -52.6 | S |
| 117 | G | -70.0 | 159.7 | S |
| 118 | P | -81.5 | 128.5 | S |
| 136 | D | -53.9 | 155.4 |   |
| 137 | K | -66.3 | -23.9 | T |
| 139 | Y | -63.0 | -45.4 | T |
| 142 | G | -71.7 | 160.4 |   |
| 166 | S | -71.6 | -69.9 |   |
| 171 | S | -61.4 | -31.2 | S |
| 173 | D | -65.5 | 0.2   | T |
| 179 | R | -65.6 | 140.0 |   |
| 214 | I | -62.9 | -56.7 | S |
| 224 | A | -65.3 | 144.7 |   |
| 239 | P | -63.3 | -26.7 |   |
| 246 | S | -64.5 | -30.6 | S |
| 248 | P | -74.3 | 159.8 | B |
| 264 | S | -69.0 | 115.0 |   |
| 266 | P | -54.6 | 134.3 |   |
| 269 | S | -88.7 | 146.3 |   |
| 275 | P | -58.3 | 138.8 |   |
| 278 | S | -88.4 | 159.0 |   |
| 282 | D | -78.1 | 153.4 |   |
| 283 | N | -60.1 | 133.4 |   |
| 284 | V | -55.6 | -28.6 | T |
| 285 | D | -72.8 | -15.7 | T |
| 297 | V | -85.1 | 157.8 | T |

Accordingly, preferred variants hold a proline residue in one or more of the following positions: 5, 8, 9, 10, 19, 38, 39, 40, 41, 44, 55, 56, 59, 61, 64, 109, 112, 117, 118, 133, 136, 137, 139, 142, 164, 166, 171, 173, 179, 196, 214, 224, 239, 246, 248, 264, 266, 269, 275, 278, 282, 283, 284, 285, 288, 289, 297.

In yet another preferred embodiment of the invention, the stabilized beta-helix structure may be obtained by scanning the x-ray structure for positions that may be mutated into cysteine residues in order for these to form disulfide bridges and thereby stabilize the structure. This can be accomplished using the SUGCYS routine in the modelling program Whatif or by a method calculating Cβ—Cβ distances (glycines are mutated to alanines in order to have a Cβ-atom), preferably between 3.6 and 4.2 Å with a minimum sequence space of 2 amino acid residues.

In yet another preferred embodiment of the invention, the stabilized beta-helix structure may be obtained by initiating molecular dynamics calculations specifying different temperatures using the x-ray structure. By comparing the output thereof, regions potentially initiating thermal unfolding may be identified. Molecular dynamics runs may be performed e.g. using CHARMm (supplied by MSI) or NAMD (supplied by the Theoretical Biophysics Group at the University of Illinois) employing the X-ray structure including crystal waters and embedded in an equilibrated box of TIP3 water molecules, using periodic boundary conditions. The calculations may consist of a heating run of 30 ps followed by 1 ns simulation, using the following set-up parameters for all dynamics calculations: A time step of 1 fs (SHAKE algorithm applied to all hydrogen bonds) and a cut-off radius of 13 Å with the gradient of the electrostatic potential reduced to zero by a force switching function applied from 8 to 12 Å and the van der Waals potential shifted to zero. The stability of the simulations can be judged by monitoring the root-mean-square displacement (RMSD) of Cα-atoms as well as of all atoms, the radius of gyration (RGYR), and the solvent accessible surface.

As mentioned above, microbial pectate lyases may exhibit a low degree of sequence homology, but do share a number of highly conserved amino acid residues: D111, either D141 or E141, and D145 (Calcium-binding aspartates (glutamate)); R194 and R199 (binding-cleft arginines); K165 (lysine) and P196 (proline). Further, the sequence region in positions 122–126 is conserved by having the residues iWvDH, wherein i and v independently of each other are isoleucine, valine or leucine (SEQ ID NO: 27). These conserved positions may form the basis for aligning any wild-type microbial pectate lyase with the *Bacillus licheniformis* pectate lyase comprising the amino acid sequence of SEQ ID NO:2 and having the structural coordinates (X-ray structure) disclosed in Appendix 1 and, in the wild-type pectate lyase), determine amino acid residues which may be optimized based on any of the methods described above. However, it should be noted that the conserved amino acid residues in positions 122–126 may be substituted without any loss of pectate lyase activity in the variant enzyme.

For example, it is contemplated that the above methods are useful for obtaining thermostabilized variants of other cell-wall degrading enzymes either having a known X-ray structure or a contemplated structure, which can be aligned with the structure in Appendix 1.Examples of crystallized cell-wall degrading enzymes with a published X-ray structure are Bacillus pectate lyases, especially *Bacillus subtilis* and *Bacillus licheniformis* pectate lyase, and *Erwinia chrysanthemi* pectate lyase. FIG. 1 shows an alignment of the amino acid sequences of *Bacillus subtilis* pectate lyase (pel_bacsu), *Bacillus licheniformis* pectate lyase (pel_bacli), and of Erwinia pectate lyase (pel_erwch), which clearly identifies target positions for amino acid substitution according to the method of the present invention. Another example of a cell-wall degrading enzyme having a structure, which can be aligned with the structure in Appendix 1, is *Bacillus agaradhaerens* pectate lyase as disclosed in WO99/27084.

Polynucleotides

Within preferred embodiments of the invention it is contemplated that an isolated polynucleotide variant of the invention will hybridize to similar sized regions of the corresponding variant of SEQ ID NO: 1, or a sequence complementary thereto, under at least medium stringency conditions, preferably high stringency conditions.

In particular polynucleotides of the invention will hybridize to a denatured double-stranded DNA probe comprising either the full variant sequence corresponding to positions 1–909 of SEQ ID NO:1 with proper sequence alterations corresponding to actual amino acid substitutions made or any probe comprising a variant subsequence thereof having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an X-ray film.

As previously noted, the isolated polynucleotides of the present invention include DNA and RNA. Methods for isolating DNA and RNA are well known in the art. DNA and RNA encoding genes of interes can be cloned in Gene Banks or DNA libraries by means of methods known in the art.

Polynucleotides encoding polypeptides having pectate lyase activity of the invention are then identified and isolated by, for example, hybridization or PCR.

Species homologues of the wild-type pectate lyase used in preparation of the pectate lyase variants of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA encoding a polypeptide having pectate lyase activity of the invention can then be isolated by a variety of methods, such as by probing with a complete or partial DNA or with one or more sets of degenerate probes based on the disclosed sequences. A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the pectate lyase cloned from *B. licheniformis*, ATCC 14580, expressed and purified as described in Materials and Methods, or by an activity test relating to a polypeptide having pectate lyase activity. Similar techniques can also be applied to the isolation of genomic clones.

The polypeptide encoding part of the DNA sequence cloned into plasmid pSJ1678 present in *Escherichia coli* DSM 11789 and/or an analogue DNA sequence of the invention may be cloned from a strain of the bacterial species *Bacillus licheniformis*, preferably the strain ATCC 14580, producing the enzyme with pectin degrading activity, or another or related organism as described herein.

Alternatively, the analogous sequence may be constructed on the basis of the DNA sequence obtainable from the plasmid present in *Escherichia coli* DSM 11789, e.g be a sub-sequence thereof, and/or by introduction of nucleotide substitutions which do not give rise to another amino acid sequence of the pectat lyase encoded by the DNA sequence, but which corresponds to the codon usage of the host organism intended for production of the enzyme, or by introduction of nucleotide substitutions which may give rise to a different amino acid sequence (i.e. a variant of the pectin degrading enzyme of the invention).

Polypeptides

The sequence of amino acids no. 1–302 of SEQ ID No 2 is a mature pectate lyase sequence corresponding to a wild-type pectate lyase from the species *Bacillus licheniformis*.

The sequence of amino acids no. 1–302 of SEQ ID No 7 is a mature pectate lyase sequence corresponding to the variant M169I+F198V of the pectate lyase from the species *Bacillus licheniformis*.

The sequence of amino acids no. 1–302 of SEQ ID No 8 is a mature pectate lyase sequence corresponding to the variant M169I+F198V+S721 of the pectate lyase from the species *Bacillus licheniformis*.

The present invention also provides pectate lyase variants of polypeptides that are substantially homologous to the polypeptides of SEQ ID NO:7 or SEQ ID NO:8 and their species homologs (paralogs or orthologs) with the proviso that the amino acid residues of the following positions of SEQ ID NO:7 or SEQ ID NO:8 are conserved: 111, 141, 145, 165, 169, 194, 196, 198 and 199. Optionally, the amino acid residues of positions 123, 125 and 126 are also conserved, but amino acid substitutions in any of these positions may be made without loss of catalytic, i.e. pectate lyase, activity. The term "substantially homologous" is used herein to denote polypeptides having 70%, more preferably at least 85%, and even more preferably at least 90%, sequence identity to the sequence shown in SEQ ID NO:7 or SEQ ID NO:8 or their orthologs or paralogs. Such polypeptides will more preferably be at least 95% identical, and most preferably 98% or more identical to the sequence shown in SEQ ID NO:7 or SEQ ID NO:8 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The wild-type pectate lyase is preferably derived from a microorganism, preferably from a bacterium, an archea or a fungus, especially from a bacterium such as a bacterium belonging to Bacillus, preferably to an alkalophilic Bacillus strain which may be selected from the group consisting of the species *Bacillus licheniformis* and highly related Bacillus species in which all species preferably are at least 95%, even more preferably at least 98%, homologous to *Bacillus licheniformis* based on aligned 16S rDNA sequences.

Substantially homologous wild-type proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions.

TABLE 1

Conservative amino acid substitutions

| | |
|---|---|
| Basic: | arginine |
| | lysine |
| Acidic: | glutamic acid |
| | aspartic acid |
| Polar: | glutamine |
| | asparagine |
| | serine |
| | threonine |
| Hydrophobic: | leucine |
| | isoleucine |
| | valine |
| Aromatic/ | phenylalanine |
| Heteroaromatic: | tryptophan |
| | tyrosine |
| | histidine |
| Small: | glycine |
| | alanine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e pectate lyase activity) to identify amino acid residues that are critical to the activity of the molecule. See also, Hilton et al., *J. Biol Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625.

Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 1:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modem equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 to 302 of SEQ ID NO: 2 and retain the pectate lyase activity of the wild-type protein.

However, the very same methods are also useful for providing the pectate lyase variants of the invention having more advantageous properties than the wild-type protein. Using these methods, the present inventors have identified a number of positions in which the wild-type pectate lyase of SEQ ID NO:2 may advantageously by substituted in order to prepare variants with improved properties.

Preferred pectate lyase variants of the inventions are substituted in one or more of the following positions (numbering relative to SEQ ID NO:2): 41, 55, 71, 72, 82, 83, 90, 100, 102, 114, 129, 133, 136, 144, 160, 163, 167, 168, 169, 189, 192, 197, 198,200, 203, 207, 220, 222, 230, 232, 236, 237, 238, 244, 246, 261, 262, 265, 269, 282, 283, 284, 285, 288 and 289.

Further examples of preferred variants are those holding a proline residue in one or more of the following positions (numbering relative to SEQ ID NO:2): 5, 8, 9, 10, 19, 38, 39, 40, 41, 44, 55, 56, 59, 61, 64, 109, 112, 117, 118, 133, 136, 137, 139, 142, 164, 166, 171, 173, 179, 196, 214, 224, 239, 246, 248, 264, 266, 269, 275, 278, 282, 283, 284, 285, 288, 289, 297.

In a preferred embodiment of the present invention, the *Bacillus licheniformis* pectate lyase variant comprises at least one substituted amino acid residue selected from the group consisting of A41P, T55P, V71N, S72I,T, L82I, K83N,H, W90H, L100N, I102F, G114N, L129F, L133N, D136A,P,S,T,V, F144V, V160F, G163L,H,I, M167F,I,S, L168N, M169I, E189H,N, N192Y, S197N, F200N, Y, G203V,A, N207S, S220,V, M222N,Y, N230E, L232N, A236V, K237N, D238N, Y244D, S246R,P, S261I, R262E, M265K, S269P, D282H, N283P, D284P, D285G, K288P and S289P. It is at present contemplated that one or more of these substitutions either alone or in combination increase the thermostability of the pectate lyase variant when compared to the wild-type enzyme.

Preferred multiple substitutions in the aliphatic and aromatic stacks of amino acid side chains believed to stabilize the β-helix structure are:

M169I+F198V
M169I+F198V+S220I
M169I+F198V+S220V
S197N+L168N
S197N+L168N+G114N
F200N+M222N
F200Y+M222Y, and other preferred substitutions in the stacks are K83N, M167F,I, E189H,N, G163L, L100N, S72I and V71N.

Preferred multiple substitutions believed to stabilize the C-terminal turn are:

N283P+D285G
D282H+N283P+D284P
D282H+N283P+D284P+K288P

Preferred multiple substitutions believed to stabilize the binding cleft are:

K237N+D238N
K237N+D238N+R262E
Y244D+S246R
N207S+N230E, and other preferred substitutions are D136Y, N192Y and R262E.

The pectate lyase variant of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the pectin degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the pectin degrading enzyme and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the pectin degrading enzyme of the invention.

Protein Production

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus agaradherens, or in particular Bacillus licheniformis.

Techniques for manipulating cloned DNA molecules and introducing exogenous DNA into a variety of host cells are disclosed by Sambrook et al., Molecular Cloning A Laboratory Manual, 2nd ed., Cold Spring Harbor Laboratory Press, Cold Spring Harbor, N.Y., 1989; Ausubel et al. (eds.), Current Protocols in Molecular Biology, John Wiley and Sons, Inc., New York, 1987; and (Bacillus subtilis and Other Gram-Positive Bacteria, Sonensheim et al., 1993, American Society for Microbiology, Washington D.C.), which are incorporated herein by reference.

In general, a DNA sequence encoding a pectate lyase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to (Bacillus subtilis and Other Gram-Positive Bacteria, Sonenshein et al., 1993, American Society for Microbiology, Washington D.C.; and Cutting, S. M.(eds.) "Molecular Biological Methods for Bacillus". John Wiley and Sons, 1990) for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The fermentation may be carried out by cultivation of the host cell under aerobic conditions in a nutrient medium containing carbon and nitrogen sources together with other essential nutrients, the medium being composed in accordance with the principles of the known art. The medium may be a complex rich medium or a minimal medium. The nitrogen source may be of inorganic and/or organic nature. Suitable inorganic nitrogen sources are nitrates and ammonium salts. Among the organic nitrogen sources quite a number are used regularly in fermentations. Examples are soybean meal, casein, corn, corn steep liquor, yeast extract, urea and albumin. Suitable carbon sources are carbohydrates or carbohydrate containing materials. Preferable the nutrient medium contains pectate, polygalacturonic acid and/or pectin esterified to a higher or lower degree as carbon source and/or inducer of pectinase production. Alternatively, the medium contains a pectin rich material such as soybean meal, apple pulp or citrus peel.

The cultivation may preferably be conducted at alkaline pH values such as at least pH 8 or at least pH 9, which can be obtained by addition of suitable buffers such as sodium carbonate or mixtures of sodium carbonate and sodium bicarbonate after sterilisation of the growth medium.

Protein Isolation

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography Principles & Methods*, Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Accordingly, in a further aspect, the present invention also relates to a method of producing the enzyme preparation of the invention, the method comprising culturing a microorganism capable of producing the pectate lyase variant under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the pectate lyase variant. The growth medium may contain a conventional N-source such as peptone, yeast extract or casamino acids, a reduced amount of a conventional C-source such as dextrose or sucrose, and an inducer such as pectate or pectin or composit plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

In yet another aspect, the present invention relates to an isolated pectate lyase variant having the properties described above and which is free from homologous impurities, and is produced using conventional recombinant techniques.

Transgenic Plants

The present invention also relates to a transgenic plant, plant part or plant cell which has been transformed with a DNA sequence encoding the pectin degrading enzyme of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana*.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285–294). Organ-specific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promotter from a seed oil body protein (Chen et al., Plant and cell physiology vol. 39, No. 9 pp. 935–941 (1998), the storage protein napA promoter from Brassica napus, or any other seed specific promoter known in the art, eg as described in WO 91/14772. Furthermore, the promoter may be a leaf specific promoter such as the rbcs promoter from nice or tomato (Kyozuka et al., Plant Physiology Vol. 102, No. 3 pp. 991–1000 (1993), the chlorella virus adenine methyltransferase gene promoter (Mitra, A. and Higgins, DW, Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol.22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well known in the art.

Enzyme Preparation

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant pectate lyase or pectate lyase variant, but which microorganism simultaneously produces other enzymes, e.g. pectin lyases, proteases, or cellulases, being naturally occurring fermentation products of the microorganism, i.e. the enzyme complex conventionally produced by the corresponding naturally occurring microorganism.

The pectate lyase variant preparation of the invention may further comprise one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are mono-component enzyme(s) which is/are mixed with the other enzyme(s) to form an enzyme preparation with the desired enzyme blend.

Immunological Cross-reactivity

Polyclonal antibodies to be used in determining immunological cross-reactivity may be prepared by use of a purified pectate lyase enzyme. More specifically, antiserum against the pectate lyase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Use in the Detergent Industry

In further aspects, the present invention relates to a detergent composition comprising the pectate lyase variant or pectate lyase variant preparation of the invention, and to a process for machine treatment of fabrics comprising treating fabric during a washing cycle of a machine washing process with a washing solution containing the pectate lyase variant or pectate lyase variant preparation of the invention.

Typically, the detergent composition of the invention comprises conventional ingredients such as surfactants (anionic, nonionic, zwitterionic, amphoteric), builders, and other ingredients, e.g. as described in WO 97/01629 which is hereby incorporated by reference in its entirety.

Use in the Textile and Cellulosic Fiber Processing Industries

The pectate lyase variant of the present invention can be used in combination with other carbohydrate degrading enzymes (for instance arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall. Or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof Examples of blends are blends of cotton or rayon/viscose with one or more companion material such as wool, synthetic fibers (e.g. polyarnide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pre-treatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like e.g. starch, CMC or PVA is added before weaving in order to increase the warp speed; This material must be removed before further processing.

b. Scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80–95° C.; and c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period, which, in the case of cold pad-batch, might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

In the examples below it is shown that the scouring step can be carried out using the pectate lyase or pectate lyase preparation of the present invention a temperature of about 50° C.–80° C. and a pH of about 7–11, thus substituting or supplementing the highly causticizing agents. An optimized enzymatic process ensures a high pectin removal and full wettability.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the pectate lyase variant of the invention.

The pectate lyase variant of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rapeseed or sunflower oil from sunflower.

The pectate lyase variant of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The pectate lyase variant of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearance of processed fruit or vegetables. The consistency and appearance has been shown to be a product of the actual combination of enzymes used for processing, i.e. the specificity of the enzymes with which the pectate lyase variant of the invention is combined. Examples include the production of clear juice e.g. from apples, pears or berries; cloud stable juice e.g. from apples, pears, berries, citrus or tomatoes; and purees e.g. from carrots and tomatoes.

The pectate lyase variant of the invention may be used in modifying the viscosity of plant cell wall derived material. For instance, the pectate lyase variant may be used to reduce the viscosity of feed containing galactan and to promote processing of viscous galactan containing material. The viscosity reduction may be obtained by treating the galactan containing plant material with an enzyme preparation of the invention under suitable conditions for full or partial degradation of the galactan containing material The pectate lyase variant can be used e.g. in combination with other enzymes for the removal of pectic substances from plant fibres. This removal is essential e.g. in the production of textile fibres or other cellulosic materials. For this purpose plant fibre material is treated with a suitable amount of the pectate lyase of the invention under suitable conditions for obtaining full or partial degradation of pectic substances associated with the plant fibre material.

Animal Feed Additive

Pectate lyase variants of the present invention may be used for modification of animal feed and may exert their effect either in vitro (by modifying components of the feed) or in vivo. The pectate lyase variant is particularly suited for addition to animal feed compositions containing high amounts of arabinogalactans or galactans, e.g. feed containing plant material from soy bean, rape seed, lupin etc. When added to the feed the pectate lyase variant significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by pectate lyase, e.g. in combination with β-galactosidase, to galactose or galactooligomers which are digestible by the animal and thus contribute to the available energy of the feed. Also, by the degradation of galactan the pectate lyase may improve the digestibility and uptake of non-carbohydrate feed constituents such as protein, fat and minerals.

For further description reference is made to PCT/DK 96/00443 and a working example herein.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

Determination of Catalytic Activity of Pectate Lyase

The Viscosity Assay APSU

APSU units: The APSU assay measures the change in viscosity of a solution of polygalacturonic acid in the absence of added calcium ions.

A 5% w/v solution of sodium polygalacturonate (Sigma P-1 879) is solubilised in 0.1 M glycine buffer, pH 10. 4 ml of this solution are preincubated for 5 min at 40 ?C. Then, 250 µl of the enzyme (or enzyme dilution) are added, after which the reaction is mixed for 10 sec on a mixer at the highest speed and incubated for 20 min at 40?C. or at another temperature.

Viscosity is measured using a MIVI 600 viscometer (Sofraser, 45700 Villemandeur, France). Viscosity is measured as mV after 10 sec. For calculation of APSU units the following standard curve is used:

| APSU/ml | mV |
|---------|-----|
| 0.00 | 300 |
| 4.00 | 276 |
| 9.00 | 249 |
| 14.00 | 227 |
| 19.00 | 206 |
| 24.00 | 188 |
| 34.00 | 177 |

-continued

| APSU/ml | mV |
|---------|-----|
| 49.00 | 163 |
| 99.00 | 168 |

Materials and Methods
Strains

Bacillus licheniformis ATCC 14580.
B.subtilis PL2306. This strain is the B.subtilis DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321) disrupted in the transcriptional unit of the known Bacillus subtilis cellulase gene, resulting in cellulase negative cells. The disruption was performed essentially as described in (Eds. A. L. Sonenshein, J. A. Hoch and Richard Losick (1993) Bacillus subtilis and other Gram-Positive Bacteria, American Society for microbiology, p.618).

Competent cells were prepared and transformed as described by Yasbin, R. E., Wilson, G. A. and Young, F. E. (1975) Transformation and transfection in lysogenic strains of Bacillus subtilis: evidence for selective induction of prophage in competent cells. J. Bacteriol, 121:296–304.
Plasmids
pMOL944

This plasmid is a pUB110 derivative essentially containing elements making the plasmid propagatable in Bacillus subtilis, kanamycin resistance gene and having a strong promoter and signal peptide cloned from the amyL gene of B. licheniformis ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of conventional genetic engineering techniques which are briefly described in the following.
Construction of pMOL944

The pUB110 plasmid (McKenzie, T. et al., 1986, Plasmid 15:93–103) was digested with the unique restriction enzyme NciI. A PCR fragment amplified from the amyL promoter encoded on the plasmid pDN1981 (P. L. Jørgensen et al., 1990, Gene, 96, p37–41.) was digested with NciI and inserted in the NciI digested pUB110 to give the plasmid pSJ2624. The two PCR primers used have the following sequences:

LWN5494 5'-GTCGCCGGGCGGCCGCTATCAATTGGTAACTGTATCTCAGC-3' (SEQ ID NO: 19)

LWN5495 5'-GTCGCCCGGGAGCTCTGATCAGGTACCAAGCTTGTCGACCTGCAGAA (SEQ ID NO: 20)
TGAGGCAGCAAGAAGAT-3'

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938 5'-GTCGGCGGCCGCTGATCACGTACCAAGCTTGTCGACCTGCAGAATG (SEQ ID NO: 21)
AGGCAGCAAGAAGAT-3'

LWN5939 5'-GTCGGAGCTCTATCAATTGGTAACTGTATCTCAGC-3' (SEQ ID NO: 22)

The plasmid pSJ2670 was digested with the restriction enzymes PstI and BclI and a PCR fragment amplified from a cloned DNA sequence encoding the alkaline amylase SP722 (disclosed in the International Patent Application published as WO95/26397 which is hereby incorporated by reference in its entirety) was digested with PstI and BclI and inserted to give the plasmid pMOL944. The two primers used for PCR amplification have the following sequence:

LWN7864 5'-AACAGCTGATCACGACTGATCTTTTAGCTTGGCAC-3' (SEQ ID NO: 23)

LWN7901 5'-AACTGCAGCCGCGGCACATCATAATGGGACAAATGGG-3' (SEQ ID NO: 24)

The primer #LWN7901 inserts a SacII site in the plasmid.
Genomic DNA Preparation Strain Bacillus licheniformis ATCC 14580 was propagated in liquid medium 3 as specified by ATCC (American Type Culture Collection, USA). After 18 hours incubation at 37° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

The pectate lyase encoding DNA sequence of the invention was PCR amplified using the PCR primer set consisting of these two oligo nucleotides:

Pecl.B.lich.upper.SacII
5'-CTA ACT GCA G<u>CC GCG GC</u>A GCT TCT GCC TTA AAC TCG GGC-3' (SEQ ID NO: 25)

Pecl.B.lich.lower.NotI
5'-GCG TTG AGA CGC <u>GCG GCC GCT</u> GAA TGC CCC GGA CGT TTC ACC-3' (SEQ ID NO: 26)

Restriction Sites SacII and NotII are Underlined.

Chromosomal DNA isolated from *B. licheniformis* ATCC 14580 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer. The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 1.0 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. 5 µg of pMOL944 and twentyfive-µl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 µg/ml of Kanamycin plates. After 18 hours incubation at 37° C. several clones were restreaked on fresh agar plates and also grown in liquid TY cultures with 10 µg/ml kanamycin and incubated overnight at 37° C. Next day 1 ml of cells were used to isolate plasmid from the cells using the Qiaprep Spin Plasmid Miniprep Kit #27106 according to the manufacturers recommendations for *B. subtilis* plasmid preparations. This plasmid DNA was used as template for DNA sequencing.

One clone containing the pectate lyase gene was kept, this clone was termed MB541, and the pectate lyase expressing plasmid was denoted pMB541.

The DNA corresponding to the mature part of the pectate lyase was characterised by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The cloned DNA sequence was expressed in *B. subtilis* and the protein that appeared in the supernatant corresponded to the mature protein represented in SEQ ID NO:2.

Media

TY (as described in Ausubel, F. M. et al. (eds.) "Current protocols in Molecular Biology". John Wiley and Sons, 1995).

LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0

BPX media is described in EP 0 506 780 (WO 91/09129).

The following examples illustrate the invention.

EXAMPLE 1

Construction of Pectate Lyase Variant (M169I, F198V)

The wild-type *B. licheniformis* pectate lyase encoded by SEQ ID NO: 1 is expressed in *B. subtilis* from a plasmid denoted pMB541, see Materials and Methods. This plasmid contains a fusion of the signal sequence from *B. licheniformis* alpha-amylase and the gene encoding the mature protein of *B. licheniformis* pectate lyase (SEQ ID NO: 2, wild-type pectate lyase), the expression of which is directed by the *B. licheniformis* alpha-amylase promoter. Further, the plasmid contains the origin of replication, ori, from plasmid pUB110 and the cat gene from plasmid pC194 conferring resistance towards chloramphenicol. A specific mutagenesis vector with a 1.2 kb pUC fragment inserted in the unique PstI restriction site located between the nucleotide sequence coding for the signal sequence and the mature, was prepared. The important features of this vector, denoted pCA134 include an origin of replication derived from the pUC plasmids, the cat gene conferring resistance towards chloramphenicol and gene coding the mature part of the wild-type *B. licheniformis* pectate lyase.

After verification of the DNA sequence in variant plasmids, the PstI-PstI fragment from pUC is removed and the remaining part of the vector is ligated and transformed into the protease- and amylase-depleted *Bacillus subtilis* strain SHA273 (described in WO92/11357 and WO95/10603) in order to express the variant enzyme.

In an attempt to improve the stability of said pectate lyase site-directed mutagenesis was carried out using the Mega-primer method as described by Sarkar and Sommer, 1990, BioTechniques 8: 404–407).

The *B. licheniformis* pectate lyase variant M169I+F198V was constructed by the use of the gene specific primer Pely01 (SEQ ID NO:4) and mutagenic primers Pely22 (SEQ ID NO:5) and Pely23 (SEQ ID NO:6) to amplify by PCR an approximately 470 bp DNA fragment from the pCA134 plasmid. The 470 bp fragment is purified from an agarose gel and used as a Mega-primer together with primer 113711 in a second PCR carried out on the same template.

The resulting approximately 1050 bp fragment is digested with restriction enzymes BclI and NotI and the resulting approximately 570 bp DNA fragment is purified and ligated with the pCA134 plasmid digested with the same enzymes. Competent *Bacillus subtilis* SHA273 (amylase and protease low) cells are transformed with the ligation, and Chloramphenicol resistant transformants are checked by DNA sequencing to verify the presence of the correct mutations on the plasmid.

Primer 113711:
5' GAAACAGCTATGACCATGATTACGCC 3'
(SEQ ID NO:3)

Primer Pely01:
5' CGACTGGCAATGCCGGGGCGG 3'
(SEQ ID NO:4)

Primer Pely22:
5' GGAAATCAATGCTGATCGGTTCATCGGACAGC 3'
(SEQ ID NO:5)

Primer Pely23:
5' CGTGTGCCGTCAGTACGTTTCGGAGGAGGC 3'
(SEQ ID NO:6)

EXAMPLE 2

Fermentation, Purification and Characterization of *Bacillus licheniformis* Pectate Lyase Variant M169I, F198V The clone obtained as described in Example 1 was grown in 25×200 ml BPX media with 10 µl/ml of Kanamycin in 500 ml two baffled shake flasks for 5 days at 37° C. at 300 rpm.

140 ml of shake flask culture fluid were diluted to 1000 ml with ion free water and applied to S-Sepharose (50 ml column equilibrated with 25 mM sodium acetate buffer pH 5.5). The pure pectate lyase variant was eluted using a NaCl gradient.

The pectate lyase variant gave a single band in SDS-PAGE of 35 kDa, exhibited 23 APSU units per mg protein, and a molar extinction coefficient of 57750.

The buffer of the pure enzyme was changed by size chromatography on a high load Superdex S200 column equilibrated with 0.1M EPPS buffer pH 8.0. DSC (Differential Scanning Calorimetry) was performed using a temperature increase of 1° C. per minute. The pure pectate lyase variant unfolds at 77° C. on a Microcalc calorimeter. In contrast hereto, the wild-type or parent pectate lyase enzyme melts at 69° C. under identical conditions (pH 8). DSC was also performed using Glycin buffer, 0.68 mM CaCl$_2$ pH 10, and the pure pectate lyase variant unfolds at 68° C. on a Microcalc calorimeter. In contrast hereto, the wild-type or parent pectate lyase enzyme melts at 60° C. under identical conditions (pH 10).

EXAMPLE 3

Construction, Fermentation, Purification and Characterization of Further *Bacillus licheniformis* Pectate Lyase Variants By using the methods described in Example 1 and 2, the *Bacillus licheniformis* pectate lyase variants (relative to SEQ ID NO:2) of Table I below were prepared and subjected to DSC (Differential Scanning Calorimetry) at pH 10 or pH 8 using a temperature increase of 1° C. per minute. The wild-type *Bacillus licheniformis* pectate lyase (SEQ ID NO:2) has a DSC unfolding temperature of 60° C. (pH 10) and 70° C. (pH 8).

TABLE I

| Variant no. | Substitutions relative to SEQ ID NO:2 | DSC unfolding temperature (° C.) pH 10 | pH 8 |
|---|---|---|---|
| 1 | M169I + F198V + E189H | 67 | |
| 2 | M169I + F198V + S72I | 72 | |
| 3 | M169I + F198V + F144V + M167I | 70.1 | |
| 4 | M169I + F198V + S72I + M265K | 75.9 | |

TABLE I-continued

| Variant no. | Substitutions relative to SEQ ID NO:2 | DSC unfolding temperature (° C.) pH 10 | pH 8 |
|---|---|---|---|
| 5 | M169I + F198V + S72I + G203V | 74.7 | |
| 6 | M169I + F19SV + S72I + K83H | 75.7 | |
| 7 | M169I + F198V + S72T | 66 | |
| 8 | M169I + F198V + M167I | 65.6 | |
| 9 | M169I + F198V + S72I + L82I + I102F + L129F + V160F | | 76.8 |
| 10 | M169I + F198V + T55P | 70.8 | |
| 11 | M169I + F198V + S269P | 68.5 | |
| 12 | D282H + N283P + D284P | 66 | |
| 13 | D282H + N283P + D284P + K288P | 66 | |
| 14 | M169I + F198V + N283P + D284P + K288P + S289P | 69.7 | |
| 15 | M169I + F198V + A41P | 65 | |
| 16 | M169I + F198V + D136P | 66.8 | |
| 17 | M169I + F198V + N283P | 66.1 | |
| 18 | M169I + F198V + D136S | 75.8 | 78.6 |
| 19 | M169I + F198V + D136T | 68.6 | |
| 20 | M169I + F198V + S72I + M265K | 75.9 | |
| 21 | M169I + F198V + S72I + K83N | 75.7 | |

Variant 1–6 and 21: stacking positive; variant 7–9: stacking neutral; variant 10–14: proline positive; variant 15–17: proline neutral; variant 18–20: other positive.

By using the methods described in Example 1 and 2, the *Bacillus licheniformis* pectate lyase variants (relative to SEQ ID NO:2) of Table II below were also prepared.

TABLE II

| Variant no. | Substitutions relative to SEQ ID NO:2 |
|---|---|
| 22 | N207S |
| 23 | N230E |
| 24 | N207S + N230E |
| 25 | M169I + F198V + V71N |
| 26 | M169I + F198V + W90H |
| 27 | M169I + F198V + L100N |
| 28 | M169I + F198V + S72I + W90H |
| 29 | M169I + F198V + S72I + G163I |
| 30 | M169I + F198V + S72I + G203A |
| 31 | M169I + F198V + S72I + F144V + 167S |
| 32 | M169I + F198V + S72I + G163I + 236V + S261I |
| 33 | N283P + D285G |

Variant no. 22–32: stacking, unknown; variant no. 33: proline, unknown

EXAMPLE 4

Pectate Lyase Treatment of Cellulosic Material: Effect of Pectate Lyase Variants vs. Wild-Type Pectate Lyase (SEQ ID NO: 2) on Residual Pectin The activity of the pectate lyase variants M 169I+F 198V, M169I+F 198V+S220V, M169I+F198V+D136A, M169I+F198V+T55P, all prepared according to Example 1, in textile preparation is determined by measuring the amount of pectin removed from the fabric after treating with the enzyme in a surfactant-buffer solution.

A. Materials

Fabric: Swatches (25.4 cm×91.4 cm) of 100% carded cotton fabric from Test Fabrics, quality 428U (242 g/m$^2$) was used.

Equipment: A Labomat (Mathis, Switzerland) was used at a liquor ratio of 12.5:1 (12 g fabric in 150 ml buffer/enzyme solution).

Pectate lyase: Each of the pectate lyase variants M169I+F198V, M169I+F198V+S220V, M169I+F198V+D136A, M169I+F198V+T55P were used, formulated in a solution containing 10 mM borate buffer and 0.2% (w/w) non-ionic surfactant (Tergitol 15-S-12 from Union Carbide) and 0.1% (w/w) Geropon SS-0-75, pH 8.2. Samples were compared based on equal protein concentrations.

B. Procedures and Results

The test fabrics were impregnated with the aqueous solution containing the pectate lyase by a determined wet pick-up between 95–100%, and incubated for 15 minutes at 90° C. followed by a continuously washing using the following rinse cycle:

Tank 1—Tap water rinse at 90° C. (overflow rinsing)
Tank 2—Tap water rinse at 90° C. (overflow rinsing)
Tank 3—Tap water rinse at 70° C. (overflow rinsing)
Tank 4—Tap water rinse at ambient temperature (overflow rinsing).

The samples were then heat dried in the pad steam range at 150° C. for 6 minutes. The pectin is measured by staining with ruthenium red dye (standard Ruthenium staining procedure EUS-SM-103) and the data transformed in to the amount of pectin remaining on cloth (% Residual Pectin, see Table III). The data shown in Table III below clearly indicates that the pectate lyase variants of the invention perform better at lower dosages than the wild-type (parent, native) pectate lyase. In contrast, maximum average pectin removal observed for pectate lyases in general are 30% and define as an excellent scouring effect on cotton.

TABLE III

Results in APSU/kg cotton

|  | Dose for 60% Pectin Removal | Dose for 70% Pectin Removal |
|---|---|---|
| Variant M169I + F198V | 182 | 531 |
| Variant M169I + F198V + S220V | 740 | 2379 |
| Variant M169I + F198V + D136A | 379 | 1179 |
| Variant M169I + F198V + T55P | 658 | 2392 |
| Wild-Type Pectate Lyase | 3117 | 7792 |

EXAMPLE 5

Construction, Fermentation, Purification and Characterization of *Bacillus agaradhaerens* Pectate Lyase Variants The wild-type *Bacillus agaradhaerens* pectate lyase is expressed in *B. subtilis* from a plasmid denoted pCA207, which is similar to pMB541 (see Materials and Methods) except for the pectate lyase gene now originating from *Bacillus agaradhaerens*. This plasmid contains a fusion of the signal sequence from *B. licheniformis* alpha-amylase and the gene encoding the mature protein of *Bacillus agaradhaerens* pectate lyase, the expression of which is directed by the *B. licheniformis* alpha-amylase promoter.

DNA fragments coding for a specific amino acid change were made using the SOE-PCR methods described by Higuchi, R. et al 1988, [Nucleic Acids Research Vol. 16 (15) p.7351–7367]. pCA207 was used as template in the reaction together with the mutagenesis primers and two primers located 5' to the Pst I site and 3' to the Cel II site, respectively. A major part of the pectate lyase gene was removed from plasmid pCA207 by digestion with the restriction enzymes Pst I and Cel II.

To obtain conjugated and pectate lyase expressing plasmids a PCR based multimerization reaction was made as described by Shafikhani, S. et al., 1997 [BioTechniques 23, 304–310]. The resulting PCR products were transformed into a protease-, amylase-, cellulase and pectate lyase-depleted *Bacillus subtilis* strain pMB1053-1 in order to express the variant enzyme. The sequence pectate lyase gene and variants were confirmed by automatic sequencing.

The *B. agaradhaerens* pectate lyase variant S82I was constructed by the use of the gene specific primers 101450 (SEQ ID NO: 9) and 6034 (SEQ ID NO: 10), and the mutagenic primers Pely174 (SEQ ID NO: 11) and Pely175 (SEQ ID NO: 12) resulting in a 1.4 kb fragment.

The *B. agaradhaerens* pectate lyase variant D93I was constructed by the use of the gene specific primers 101450 and 6034, and the mutagenic primers Pely176 (SEQ ID NO: 13) and Pely177 (SEQ ID NO: 14) resulting in an 1.4 kb fragment.

The *B. agaradhaerens* pectate lyase variant M179I was constructed by the use of the gene specific primers 101450 and 6034, and the mutagenic primers Pely178 (SEQ ID NO: 15) and Pely179 (SEQ ID NO: 16) resulting in an 1.4 kb fragment.

Primer 101450:
5' CATGGTGAACCAAAGTGAAACC 3'
(SEQ ID NO:9)

Primer 6034:
5' GGAAGAAAATATAGGGAAAATGG 3'
(SEQ ID NO:10)

Primer Pely174:
5' GAAATTAAAAACATCATTATTATCGGTGTAG 3'
(SEQ ID NO:11)

Primer Pely175:
5' CTACACCGATAATAATGATGGTTTTAATTTC 3'
(SEQ ID NO:12)

Primer Pely176:
5' CAAATGGAGAGTTCCATGGCATTGGGATAAG 3'
(SEQ ID NO:13)

Primer Pely177:
5' CTTATCCCAATGCCATGGAACTCTCCATTTG 3'
(SEQ ID NO:14)

Primer Pely178:
5' CATTGGAAAACTATCCTCGTCGGTCATAC 3'
(SEQ ID NO:15)

Primer Pely179:
5' GTATGACCGACGAGGATAGTTTTCCAATG 3'
(SEQ ID NO:16)

200 ml of shake flask culture fluid were diluted to 500 ml with ion free water and applied to Q-Sepharose (50 ml column equilibrated with 25 mM Tris(hydroxymethyl) amino-methane buffer, pH 8.0). The pure pectate lyase variant was eluted using a NaCl gradient.

The pectate lyase variant gave a single band in SDS-PAGE of 36 kDa.

By using the methods described in Examples 1 and 2, the *Bacillus agaradhaerens* pectate lyase variant (numbering relative to SEQ ID NO: 2) of Table IV below was prepared and subjected to DSC (Differential Scanning Calorimetry) at pH 8 using a temperature increase of 1° C. per minute. The wild-type *Bacillus agaradhaerens* pectate lyase has a DSC unfolding temperature of 60.1° C. at pH 8.

TABLE IV

| Substitution relative to SEQ ID NO:2 | DSC unfolding temperature (° C.) pH 8 |
|---|---|
| S72I | 70.4 |

EXAMPLE 6
Construction, Fermentation, Purification and Characterization of *Bacillus subtilis* Pectate Lyase Variant By using the methods described in Example 1 and 2, the *Bacillus subtilis* pectate lyase stack variant C199N (numbering relative to SEQ ID NO:2) of Table V below was prepared and subjected to DSC (Differential Scanning Calorimetry) at pH 8 using a temperature increase of 1° C. per minute. The wild-type *Bacillus subtilis* pectate lyase (Nasser et al.: Cloning of a pectate lyase from *Bacillus subtilis* (1993) FEBS 335:319–326, which is hereby incorporated by reference in its entirety) has a DSC unfolding temperature of 61.1° C. at pH 8.

TABLE I

| Pectate Lyase Variant | Substitution in position relative to SEQ ID NO:2 [substitution relative to wt *B. subtilis* pectate lyase numbering, FEBS 335:319–326 (1993)] | DSC unfolding temperature (° C.) pH 8 |
|---|---|---|
| | 127 [C199N] | 61.9 |

EXAMPLE 7
Determination of Stack Positions in *Bacillus licheniformis* Pectate Lyase Stack positions in the pectate lyase prepared in example 1 and 2 were determined based on the following rules:
  (i) the residue is part of a β-sheet—according to the output of the DSSP program and
  (ii) the β-strand is part of a sheet composed of more than two β-strands OR
  (iii) the residue is without secondary structure but is linking two β-sheet regions horizontally
  (iv) or the residue is part of a T2 turn composed by no more than two amino acid residues
  (v) or the residue has a C$_\alpha$-atom in line with an already determined stack (i.e. visually it is clearly part of the stack)

Results:
3. In: V24, I47, I73, I97, V124, F155, F183, I205, I228, V253
2. Out: T23, K46, S72, I96, W123, T154, T182, H204, R227, H252
1. In: Q22, L45, V71, I95, I122, I153, I181, G203, I226, W251
17. Out: N70, N94, N121, Y152, T180, E202, R225, Y250
16. Out: S69, N93, K120, E151
18. Out: V68, A92, S119, A150
15. Out: K66, W90, E116, K147
14. In: V65, 189, I115, V146, M169, F198, S220
13. Out: D64, K88, G114, D145, L168, S197, N219, V241
12. In: I63, I87, I113, F144, M167, P196, I218, I240
11. In: G163, L191, I213, A236, S261
10. Out: E104, -, D162, N190, K212, N235, N260
9. Out: T54, K83, H103, Y130, H161, E189, N211, E234, V259
8. In: I53, L82, I102, L129, V160, F188, F210, F233, F258
7. Out: T52, E81, K101, E128, Y159, W187, Y209, L232, K257
6. In: L100, N127, N158, N186, N208, N231, N256
5. Out: N99, H126, W157, HI 85, N207, N230, N255
4. Out: T25, Y48, V74, R98, D125, S156, H184, Y206, E229, S254

The underlined residues are conserved residues believed to be part of the active site—these would not be chosen for optimisation.

The majority of the residues are classified as stack residues based on rule a.

M167 and P196 are classified according to rule c.

S261, E104, N260, and T54 are classified according to rule e.

Stacks #5 and #6 are classified according to rule d.

Some residues are β-strand residues may not be regarded as stack-residues: 26, 49, 67, 75, 91, 164, 165, 192, 193, 199, and 221.

The sequence below (SEQ ID NO: 2) depicts the stacks—placed such that the stack residues are on top of each other; the stacks are numbered according to the list above.

```
                   ADFSLKGFAALNGGTTGGEGGQ 2 4 6         8 10                  1315              17
           1 3 5         7 9 11                1214  18          16

-TVT--VTTGDQ-------LIAA------------L----KNKNANTP
           LKIY--VNG----TIT---TSNTSASK------IDVK-DV----------SN
           VSIV--GSGTKG-ELK----GIG----------IKIW-RA----------NN
           IIIRNL-------KIHE--VASGDKDA------IGIEGPS----------KN
           IWVDHN-------ELY---HSLNVDKDYYDGL-FDVKRDA----------EY
           ITFSWN-------YVHDG-WKS-----------MLM----GSSDSDNYNR-T
           ITFHHN-------WFENL-NSRV----------PSF----RFG--------E
           GHIYNN-------YFNKI-IDSG----------INS----RMGA-------R
           IRIENN-------LFENA-KDP-----------I------VSWYSSSPGY
           WHVSNN-------KFVNS-RGSMP----------------TT

STTTYNPPYSYSLDNVDNVKSIVKQNAGVGKINP
```

What is claimed is:

1. A variant of a parent pectate lyase (EC 4.2.2.2) having the conserved amino acid residues D111, W123, D125, H126, D141 or E141, D145, K165, R194 and R199 when aligned with a pectate lyase comprising the amino acid sequence of SEQ ID NO: 2, wherein the variant comprises a substitution in at least one position selected from the group consisting of 55, 72, 83, 136, 144, 169, 198, 203, 220, 265, 269, 282, and 284, wherein the variant has pectate lyase activity.

2. The variant of claim 1, wherein the parent pectate lyase has an amino acid sequence of SEQ ID NO: 2.

3. The variant of claim 1, comprising a substitution at position 55.

4. The variant of claim 1, comprising a substitution at position 72.

5. The variant of claim 1, comprising a substitution at position 83.

6. The variant of claim 1, comprising a substitution at position 136.

7. The variant of claim 1, comprising a substitution at position 144.

8. The variant of claim 1, comprising a substitution at position 169.

9. The variant of claim 1, comprising a substitution at position 198.

10. The variant of claim 1, comprising a substitution at position 203.

11. The variant of claim 1, comprising a substitution at position 220.

12. The variant of claim 1, comprising a substitution at position 265.

13. The variant of claim 1, comprising a substitution at position 269.

14. The variant of claim 1, comprising a substitution at position 282.

15. The variant of claim 1, comprising a substitution at position 284.

16. The variant of claim 1 comprising at least one or more of the following substitutions: T55P, S72I,T, K83H,N, D136A,P,S,T,V, F144V, M169I, F198V, G203A,V, S220V, M265K, S269P, D282H, and D284P.

17. The variant of claim 1, comprising the amino acid sequence of SEQ ID NO: 7.

18. The variant of claim 1, comprising the amino acid sequence of SEQ ID NO: 8.

19. The variant of claim 16, comprising one of the following:
S72I+M169I+F198V; or
F144V+M167I+M169I+F198V; or
M169I+E189H+F198V.

20. The variant of claim 19, comprising one of the following:
S72I+K83H+M169I+F198V; or
S72I+M169I+F198V+G203V; or
S72I+M169I+F198V+M265K.

21. The variant of claim 16, comprising one of the following:
S72I+L82I+I102F+L129F+V160F+M169I+F198V; or
S72T+M169I+F198V; or
M167I+M169I+F198V.

22. The variant of claim 16, comprising one of the following:
V71N+M169I+F198V; or
S72I+W90H+M169I+F198V; or
S72I+G163I+M169I+F198V; or
S72I+M169I+F198V+G203A; or
S72I+F144V+M167S+M169I+F198V; or
S72I+G163I+M169I+F198V+A236V+S261I; or
W90H+M169I+F198V; or
L100N+M169I+F198V.

23. The variant of claim 16, comprising one of the following:
T55P+M169I+F198V; or
M169I+F198V+S269P; or
M169I+F198V+N283P+D284P+K288P+S289P; or
D282H+N283P+D284P; or
D282H+N283P+D284P+K288P.

24. The variant of claim 16, comprising one of the following:
A41P+M169I+F198V; or
D136P+M169I+F198V; or
M169I+F198V+N283P; or
N283P+D285G.

25. The variant of claim 16, comprising one of the following:
S72I+M169I+F198V+M265K; or
S72I+K83N+M169I+F198V; or
D136S+M169I+F198V; or
D136T+M169I+F198V.

26. A detergent composition comprising the variant of claim 1 and a surfactant.

27. The detergent composition of claim 26, which further comprises one or more enzymes selected from the group consisting of alpha-amylases, arabinosidases, cellulases (endoglucanases), cellobiohydrolases, cutinases, galactanases, beta-glucanases, glucoamylases, hemicellulases, laccases, ligninases, lipases, mannanases, oxidases, pectin acetyl esterases, pectinases, pectin lyases, pectin methylesterases, peroxidases, phenoloxidases, polygalacturonases, proteases, reductases, pullulanases, rhamnogalacturonases, transglutaminases, xylanases, xyloglucanases, other pectate lyases, or mixtures thereof.

28. A variant of a parent pectate lyase (EC 4.2.2.2) having the conserved amino acid residues corresponding to D111, W123, D125, H126, D141, or E141, D145, K165, R194, and R199 of SEQ ID NO: 2 when aligned with a pectate lyase comprising the amino acid of SEQ ID NO: 2, wherein the variant comprises a substitution in a lease one position corresponding to a position in SEQ ID NO: 2 selected from the group consisting of 55, 72, 83, 136, 144, 169, 198, 203, 220, 265, 269, 282, and 284, wherein the variant has pectate lyase activity. claim 1.

29. The method of claim 28, wherein the variant is used in a scouring process step.

30. A method for degradation or modification of plant material, comprising treating the plant material with an effective amount of the variant of claim 1.

31. The method of claim 30, wherein the plant material is recycled waste paper, mechanical paper-making pulps or fibers subjected to a retting process.

* * * * *

SEQUENCE LISTING

<160> NUMBER OF SEQ ID NOS: 8

<210> SEQ ID NO 1
<211> LENGTH: 909
<212> TYPE: DNA
<213> ORGANISM: Bacillus licheniformis

<400> SEQUENCE: 1

```
gccgacttca gcttaaaagg ctttgccgca ctaaacggcg gaacaacggg cggagaaggc      60
ggtcagacgg taaccgtaac aacgggagat cagctgattg cggcattaaa aaataagaat    120
gcaaatacgc ctttaaaaat ttatgtcaac ggcaccatta aacatcaaa tacatccgca     180
tcaaagattg acgtcaaaga cgtgtcaaac gtatcgattg tcggatcagg gaccaaaggg    240
gaactcaaag ggatcggcat caaaatatgg cgggccaaca acatcatcat ccgcaacttg    300
aaaattcacg aggtcgcctc aggcgataaa gacgcgatcg gcattgaagg cccttctaaa    360
aacatttggg ttgatcataa tgagctttac cacagcctga acgttgacaa agattactat    420
gacggattat ttgacgtcaa aagagatgcg gaatatatta cattctcttg gaactatgtg    480
cacgatggat ggaaatcaat gctgatgggt tcatcggaca gcgataatta acaggacg     540
attacattcc atcataactg gtttgagaat ctgaattcgc gtgtgccgtc attccgtttc    600
ggagaaggcc atatttacaa caactatttc aataaaatca tcgacagcgg aattaattcg    660
aggatgggcg cgcgcatcag aattgagaac aacctctttg aaaacgccaa agatccgatt    720
gtctcttggt acagcagttc accgggctat tggcatgtat ccaacaacaa atttgtaaac    780
tctagggca gtatgccgac tacctctact acaacctata atccgccata cagctactca    840
ctcgacaatg tcgacaatgt aaaatcaatc gtcaagcaaa atgccggagt cggcaaaatc    900
aatccataa                                                             909
```

<210> SEQ ID NO 2
<211> LENGTH: 302
<212> TYPE: PRT
<213> ORGANISM: Bacillus licheniformis

<400> SEQUENCE: 2

Ala Asp Phe Ser Leu Lys Gly Phe Ala Ala Leu Asn Gly Gly Thr Thr
1               5                  10                  15

Gly Gly Glu Gly Gly Gln Thr Val Thr Val Thr Thr Gly Asp Gln Leu
            20                  25                  30

Ile Ala Ala Leu Lys Asn Lys Asn Ala Asn Thr Pro Leu Lys Ile Tyr
        35                  40                  45

Val Asn Gly Thr Ile Thr Thr Ser Asn Thr Ser Ala Ser Lys Ile Asp
    50                  55                  60

Val Lys Asp Val Ser Asn Val Ser Ile Val Gly Ser Gly Thr Lys Gly
65                  70                  75                  80

Glu Leu Lys Gly Ile Gly Ile Lys Ile Trp Arg Ala Asn Asn Ile Ile
                85                  90                  95

Ile Arg Asn Leu Lys Ile His Glu Val Ala Ser Gly Asp Lys Asp Ala
            100                 105                 110

Ile Gly Ile Glu Gly Pro Ser Lys Asn Ile Trp Val Asp His Asn Glu
        115                 120                 125

Leu Tyr His Ser Leu Asn Val Asp Lys Asp Tyr Tyr Asp Gly Leu Phe
    130                 135                 140

-continued

Asp Val Lys Arg Asp Ala Glu Tyr Ile Thr Phe Ser Trp Asn Tyr Val
145                 150                 155                 160

His Asp Gly Trp Lys Ser Met Leu Met Gly Ser Ser Asp Ser Asp Asn
                165                 170                 175

Tyr Asn Arg Thr Ile Thr Phe His His Asn Trp Phe Glu Asn Leu Asn
            180                 185                 190

Ser Arg Val Pro Ser Phe Arg Phe Gly Glu Gly His Ile Tyr Asn Asn
        195                 200                 205

Tyr Phe Asn Lys Ile Ile Asp Ser Gly Ile Asn Ser Arg Met Gly Ala
    210                 215                 220

Arg Ile Arg Ile Glu Asn Asn Leu Phe Glu Asn Ala Lys Asp Pro Ile
225                 230                 235                 240

Val Ser Trp Tyr Ser Ser Pro Gly Tyr Trp His Val Ser Asn Asn
                245                 250                 255

Lys Phe Val Asn Ser Arg Gly Ser Met Pro Thr Thr Ser Thr Thr Thr
                260                 265                 270

Tyr Asn Pro Pro Tyr Ser Tyr Ser Leu Asp Asn Val Asp Asn Val Lys
            275                 280                 285

Ser Ile Val Lys Gln Asn Ala Gly Val Gly Lys Ile Asn Pro
    290                 295                 300

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
gaaacagcta tgaccatgat tacgcc                                            26

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
cgactggcaa tgccggggcg g                                                 21

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
ggaaatcaat gctgatcggt tcatcggaca gc                                     32

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cgtgtgccgt cagtacgttt cggaggaggc                                        30

```
<210> SEQ ID NO 7
<211> LENGTH: 302
<212> TYPE: PRT
<213> ORGANISM: Artificial Sequence
<220> FEATURE:
<223> OTHER INFORMATION: Synthetic

<400> SEQUENCE: 7

Ala Asp Phe Ser Leu Lys Gly Phe Ala Ala Leu Asn Gly Gly Thr Thr
1               5                   10                  15

Gly Gly Glu Gly Gly Gln Thr Val Thr Val Thr Gly Asp Gln Leu
            20                  25                  30

Ile Ala Ala Leu Lys Asn Lys Asn Ala Asn Thr Pro Leu Lys Ile Tyr
                35                  40                  45

Val Asn Gly Thr Ile Thr Thr Ser Asn Thr Ser Ala Ser Lys Ile Asp
    50                  55                  60

Val Lys Asp Val Ser Asn Val Ser Ile Val Gly Ser Gly Thr Lys Gly
65                  70                  75                  80

Glu Leu Lys Gly Ile Gly Ile Lys Ile Trp Arg Ala Asn Asn Ile Ile
                85                  90                  95

Ile Arg Asn Leu Lys Ile His Glu Val Ala Ser Gly Asp Lys Asp Ala
                100                 105                 110

Ile Gly Ile Glu Gly Pro Ser Lys Asn Ile Trp Val Asp His Asn Glu
            115                 120                 125

Leu Tyr His Ser Leu Asn Val Asp Lys Asp Tyr Asp Gly Leu Phe
130                 135                 140

Asp Val Lys Arg Asp Ala Glu Tyr Ile Thr Phe Ser Trp Asn Tyr Val
145                 150                 155                 160

His Asp Gly Trp Lys Ser Met Leu Ile Gly Ser Ser Asp Ser Asp Asn
                165                 170                 175

Tyr Asn Arg Thr Ile Thr Phe His His Asn Trp Phe Glu Asn Leu Asn
                180                 185                 190

Ser Arg Val Pro Ser Val Arg Phe Gly Glu Gly His Ile Tyr Asn Asn
            195                 200                 205

Tyr Phe Asn Lys Ile Ile Asp Ser Gly Ile Asn Ser Arg Met Gly Ala
210                 215                 220

Arg Ile Arg Ile Glu Asn Asn Leu Phe Glu Asn Ala Lys Asp Pro Ile
225                 230                 235                 240

Val Ser Trp Tyr Ser Ser Pro Gly Tyr Trp His Val Ser Asn Asn
                245                 250                 255

Lys Phe Val Asn Ser Arg Gly Ser Met Pro Thr Thr Ser Thr Thr Thr
                260                 265                 270

Tyr Asn Pro Pro Tyr Ser Tyr Ser Leu Asp Asn Val Asp Asn Val Lys
                275                 280                 285

Ser Ile Val Lys Gln Asn Ala Gly Val Gly Lys Ile Asn Pro
            290                 295                 300

<210> SEQ ID NO 8
<211> LENGTH: 302
<212> TYPE: PRT
<213> ORGANISM: Artificial Sequence
<220> FEATURE:
<223> OTHER INFORMATION: Synthetic

<400> SEQUENCE: 8

Ala Asp Phe Ser Leu Lys Gly Phe Ala Ala Leu Asn Gly Gly Thr Thr
1               5                   10                  15
```

-continued

```
Gly Gly Glu Gly Gly Gln Thr Val Thr Val Thr Thr Gly Asp Gln Leu
            20              25              30

Ile Ala Ala Leu Lys Asn Lys Asn Ala Asn Thr Pro Leu Lys Ile Tyr
            35              40              45

Val Asn Gly Thr Ile Thr Thr Ser Asn Thr Ser Ala Ser Lys Ile Asp
 50              55              60

Val Lys Asp Val Ser Asn Val Ile Ile Val Gly Ser Gly Thr Lys Gly
 65              70              75              80

Glu Leu Lys Gly Ile Gly Ile Lys Ile Trp Arg Ala Asn Asn Ile Ile
                85              90              95

Ile Arg Asn Leu Lys Ile His Glu Val Ala Ser Gly Asp Lys Asp Ala
            100             105             110

Ile Gly Ile Glu Gly Pro Ser Lys Asn Ile Trp Val Asp His Asn Glu
            115             120             125

Leu Tyr His Ser Leu Asn Val Asp Lys Asp Tyr Tyr Asp Gly Leu Phe
            130             135             140

Asp Val Lys Arg Asp Ala Glu Tyr Ile Thr Phe Ser Trp Asn Tyr Val
145             150             155             160

His Asp Gly Trp Lys Ser Met Leu Ile Gly Ser Ser Asp Ser Asp Asn
                165             170             175

Tyr Asn Arg Thr Ile Thr Phe His His Asn Trp Phe Glu Asn Leu Asn
                180             185             190

Ser Arg Val Pro Ser Val Arg Phe Gly Glu Gly His Ile Tyr Asn Asn
            195             200             205

Tyr Phe Asn Lys Ile Ile Asp Ser Gly Ile Asn Ser Arg Met Gly Ala
            210             215             220

Arg Ile Arg Ile Glu Asn Asn Leu Phe Glu Asn Ala Lys Asp Pro Ile
225             230             235             240

Val Ser Trp Tyr Ser Ser Pro Gly Tyr Trp His Val Ser Asn Asn
            245             250             255

Lys Phe Val Asn Ser Arg Gly Ser Met Pro Thr Thr Ser Thr Thr Thr
            260             265             270

Tyr Asn Pro Pro Tyr Ser Tyr Ser Leu Asp Asn Val Asp Asn Val Lys
        275             280             285

Ser Ile Val Lys Gln Asn Ala Gly Val Gly Lys Ile Asn Pro
        290             295             300
```